United States Patent [19]

Fukui et al.

[11] Patent Number: 4,801,445

[45] Date of Patent: Jan. 31, 1989

[54] COSMETIC COMPOSITIONS CONTAINING MODIFIED POWDER OR PARTICULATE MATERIAL

[75] Inventors: Hiroshi Fukui; Ryujiro Namba; Tsutomu Saito; Yutaka Ohtsu; Asa Kimura; Motokiyo Nakano; Okitsugu Nakata; Kenichi Tomita; Kazuo Tokubo; Kazuhisa Ohno; Toshio Yoneyama; Takashi Ogawa; Hideo Morohoshi; Junichi Koyama; Taketoshi Kanda; Kunihiro Kawaguchi; Yuzo Shimizu, all of Yokohama, Japan

[73] Assignee: Shiseido Company Ltd., Tokyo, Japan

[21] Appl. No.: 875,140

[22] Filed: Jun. 17, 1986

[30] Foreign Application Priority Data

| Jul. 29, 1985 | [JP] | Japan | 60-165974 |
| Sep. 3, 1985 | [JP] | Japan | 60-194654 |
| Nov. 15, 1985 | [JP] | Japan | 60-256166 |
| Nov. 26, 1985 | [JP] | Japan | 60-265715 |
| Feb. 5, 1986 | [JP] | Japan | 61-023518 |
| Feb. 18, 1986 | [JP] | Japan | 61-033595 |
| Mar. 25, 1986 | [JP] | Japan | 61-066635 |
| Apr. 3, 1986 | [JP] | Japan | 61-077301 |
| Apr. 3, 1986 | [JP] | Japan | 61-077302 |
| Apr. 5, 1986 | [JP] | Japan | 61-078740 |
| Apr. 5, 1986 | [JP] | Japan | 61-078741 |
| May 9, 1986 | [JP] | Japan | 61-106175 |
| May 23, 1986 | [JP] | Japan | 61-118901 |
| May 28, 1986 | [JP] | Japan | 61-122821 |
| May 31, 1986 | [JP] | Japan | 61-127047 |
| Jun. 10, 1986 | [JP] | Japan | 61-134540 |
| Jun. 13, 1986 | [JP] | Japan | 61-137838 |
| Jun. 13, 1986 | [JP] | Japan | 61-137839 |
| Jun. 13, 1986 | [JP] | Japan | 61-137840 |
| Jun. 13, 1986 | [JP] | Japan | 61-137841 |

[51] Int. Cl.$^4$ ............... A61K 7/021; A61K 7/032; A61K 7/035

[52] U.S. Cl. .................... 424/69; 424/63; 424/78; 428/403; 428/404; 428/405; 428/407; 514/844; 523/209; 523/213; 523/215; 523/216

[58] Field of Search ............... 424/69, 78, 63; 428/403, 405, 407, 404; 523/209, 213, 215, 216, 212; 514/844

[56] References Cited

U.S. PATENT DOCUMENTS

| 3,649,321 | 3/1972 | Durrant et al. | 523/212 |
| 3,849,152 | 11/1974 | Mimeault | 106/308 Q |
| 3,920,865 | 11/1975 | Läufer et al. | 428/405 |
| 4,034,139 | 7/1977 | Mazargull et al. | 428/405 |
| 4,062,693 | 12/1977 | Berger | 428/405 |
| 4,151,154 | 4/1979 | Berger | 428/405 |
| 4,191,587 | 3/1980 | Kratel et al. | 106/308 Q |
| 4,394,469 | 7/1983 | Stratta et al. | 523/213 |
| 4,578,266 | 3/1986 | Tietjen et al. | 424/63 |

Primary Examiner—Allan M. Lieberman
Attorney, Agent, or Firm—Sprung Horn Kramer & Woods

[57] ABSTRACT

A modified powder or particulate material having a silicone polymer film coated on substantially the entire surface thereof, this powder or particulate material being produced by bringing at least one silicone compound, in the form of a vapor, having the general formula (I):

$$(R^1HSiO)_a(R^2R^3SiO)_b(R^4R^5R^6SiO_{\frac{1}{2}})_c \qquad (I)$$

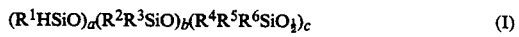

wherein $R^1$, $R^2$, and $R^3$ represent, independently, hydrogen or a hydrocarbon residue having 1 to 10 carbon atoms, which may be substituted with at least one halogen atom, provided that $R^1$, $R^2$, and $R^3$ are not hydrogen at the same time, $R^4$, $R^5$, and $R^6$ represent, independently, hydrogen or a hydrocarbon residue having 1 to 10 carbon atoms, which may be substituted with at least one halogen atom, a is zero or an integer of 1 or more, b is zero or an integer of 1 or more, and c is zero or 2, provided that c is 2 when a and b are simultaneously zero and a+b is an integer of 3 or more when c is zero, into contact with a powder or particulate material having an active site on the surface thereof, whereby the silicone compound is polymerized on substantially the entire surface of the powder or particulate material.

21 Claims, 5 Drawing Sheets

NON-TREATMENT    EXAMPLE

NON-TREATMENT    EXAMPLE

COSMETIC COMPOSITIONS CONTAINING MODIFIED POWDER OR PARTICULATE MATERIAL

BACKGROUND OF THE INVENTION

1. Field of the Invention

The present invention relates to a modified powder or particulate material having a silicone polymer film coated on substantially the entire surface thereof. More specifically, it relates to a modified powder or particulate material obtained by treating a powder or particulate material having active sites on the surface thereof with a certain silicone compound in the form of a vapor, whereby the surface activities of the powder or particulate material are made to disappear. The term "powder or particulate material" (i.e., "powder material" hereinbelow) used herein means any material generally having a particle size of 10 mm or less, but sometimes more than 10 mm. The agglomerates and the molded or shaped products of the powder are also included in this term. The term "active site" used herein means those capable of catalytically polymerizing a silicone compound having a siloxane bond (Si—O—Si) or a hydrosilyl group (Si-H) (i.e., acidic, basic, oxidative, or reductive sites).

The modified powder material according to the present invention does not denature or decompose perfumes, oils, or resins even when coexisting therewith, and therefore, will not cause problems such as denaturation, odor change, and color change and can be utilized in the fields of, for example, cosmetics, pharmaceuticals, coating materials, inks, paints, decoratives, fragrants, magnetic materials, and medical materials.

2. Description of the Related Art

Silicone oils have been frequently used in the prior art for the hydrophobic modification of a powder material. For example, Japanese Examined Patent Publication (Kokoku) No. 41-9890 discloses imparting lubricity to an animal, vegetable or mineral powder by coating the surface of the powder with a silicone resin coating material, followed by drying and baking. In Japanese Examined Patent Publication (Kokoku) No. 45-2915, a mineral powder such as talc is simply attached with a silicone having hydrogen directly bonded to silicone in the molecular chain by, for example, blender mixing, followed by heating baking, thereby imparting a water repellency to the powder. According to Japanese Examined Patent Publication (Kokoku) No. 45-18999, talc is attached with dimethylpolysiloxane or methylhydrogenpolysiloxane by contact with an organic solvent solution thereof, followed by baking optionally with the addition of a substance such as zinc octoate as the cross linking polymerization catalyst for methylhydrogenpolysiloxane, thereby imparting a free flow property to the powder. Further, in Japanese Examined Patent Publication (Kokoku) No. 49-1769, titanium dioxide is subjected to direct coating, emulsion coating or solvent solution coating of various alkylpolysiloxanes, and then dried and baked optionally by using, in combination, an ester compound having a total carbon number of 6 or more, whereby the dust property, dispersibility, etc., of the powder are modified. On the other hand, in Japanese Unexamined Patent Publications (Kokai) Nos. 56-16404, 55-136213 and 56-29512, after mixing under stirring with the addition of silicone oils and oil agents or by the application of a mechanochemical reaction such as crushing, a baking treatment is performed.

Further, Japanese Unexamined Patent Publication (Kokai) No. 57-200306 discloses a method for imparting a water repellency and flow property to a powder without the application of a baking treatment by treating the powder with (A) a silane compound having a specific structure, (B) a cyclic polyorganosiloxane, and (C) a linear polyorganosiloxane. According to this method, 1 to 10% by weight based on the powder to be treated of the above organic silicone compound is adsorbed onto the powder by spraying a solution diluted in a solvent, direct spraying, or gaseous atomization, or by directly mixing under stirring, and then a water or water vapor treatment is applied. In the (B) cyclic polyorganosiloxane, the trimer having a methyl group is excluded, because it is solid and difficult to handle.

However, according to these methods, in most organic pigments and inorganic pigments, those weakly resistant to heat, such as yellow iron oxide or prussian blue, could not be treated.

For example, among the organic pigments, C.I. 15850:1 (lithol rubine BCA) could not be treated, because it was dehydrated at 80° C. and changed crystal form from $\alpha$-type to $\beta$-type simultaneously with a change in tone. On the other hand, prussian blue is decomposed by the application of heat and gradually releases cyan gas at 150° C. or higher. Baking treatment is carried out at 350° C. for 2 hours, as a typical example of a higher temperature treatment, or at 150° C. for 15 to 40 hours, as a typical example of a lower temperature treatment. Under such conditions, prussian blue not only undergoes a color change but also releases harmful cyan gas, thus being very dangerous.

Such a baking treatment of the prior art can be applied only for a part of stable inorganic pigments, and has the vital defect that treatment of an organic pigment which is brilliant among pigments impaired the tone of its color.

Indeed, treatment at a lower temperature is possible when a catalyst is used for lowering the baking temperature, but the catalyst remained, to promote deterioration of the silicone resin on the surface, and cause marked changes with a lapse of time. Thus, this method had little success in practical application, as a general rule. Also, the catalyst not only affects the silicone resin on the surface but also promotes decomposition of coexisting components such as oils or perfumes to cause the problems of denaturation or change of odor, etc., and therefore, it could not be used for cosmetics, etc.

Japanese Unexamined Patent Publication (Kokai) No. 56-16404 discloses a silicone treatment method utilizing a mechanochemical reaction. According to this method, because a crushing force is utilized, powder specifically shaped into plates or spheres suffers from a change in shape. Also, for a powder such as titanium dioxide, which will be agglomerated by stirring, even the treatment of it alone could be done only with difficulty.

In Japanese Unexamined Patent Publication (Kokai) No. 57-200306, in any case, the treating agent does not come into contact with the powder in the form of molecules but in the form of liquid or fine particles of liquid. For this reason, the trimer, which is solid, is excluded from cyclic polyorganosiloxanes. The amount of the treating agent is defined as 1 to 10% based on the powder, but such an amount may be insufficient depending on the kind of powder, whereby the surface activity of the powder remains and the stability of a perfume, if co-present, will be disadvantageously worsened.

SUMMARY OF THE INVENTION

Accordingly, the object of the present invention is to eliminate the above-mentioned disadvantages of the prior art and to provide a modified powder or particulate material having improved properties including hydrophobic nature and stability with a disappearance of the surface activities thereof (i.e., not capable of denaturing or decomposing other substances if co-existing) and with maintaining the inherent characteristics of the powder or particulate material to be modified.

Other objects and advantages of the present invention will be apparent from the following description.

In accordance with the present invention, there is provided a modified powder or particulate material having a silicone polymer film coated on substantially the entire surface thereof, this powder or particulate material being produced by bringing at least one silicone compound, in the form of a vapor, having the general formula (I):

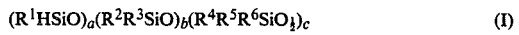

$$(R^1HSiO)_a(R^2R^3SiO)_b(R^4R^5R^6SiO_{\frac{1}{2}})_c \qquad (I)$$

wherein $R^1$, $R^2$, and $R^3$ represent, independently, hydrogen or a hydrocarbon residue having 1 to 10 carbon atoms, which may be substituted with at least one halogen atom, provided that $R^1$, $R^2$, and $R^3$ are not hydrogen at the same time, $R^4$, $R^5$, and $R^6$ represent, independently, hydrogen or a hydrocarbon residue having 1 to 10 carbon atoms, which may be substituted with at least one halogen atom, a is zero or an integer of 1 or more, b is zero or an integer of 1 or more, and c is zero or 2, provided that c is 2 when a and b are simultaneously zero and a+b is an integer of 3 or more when c is zero, and preferably a+b+c is 3 to 10, into contact with a powder or particulate material having an active site on the surface thereof, whereby the silicone compound is polymerized on substantially the entire surface of the powder or particulate material.

BRIEF DESCRIPTION OF THE DRAWINGS

The present invention will be better understood from the description set forth below with reference to the accompanying drawings illustrating, but not intended to be limited to, the preferred embodiments of the present invention, in which.

DESCRIPTION OF THE PREFERRED EMBODIMENTS

Figure 1:
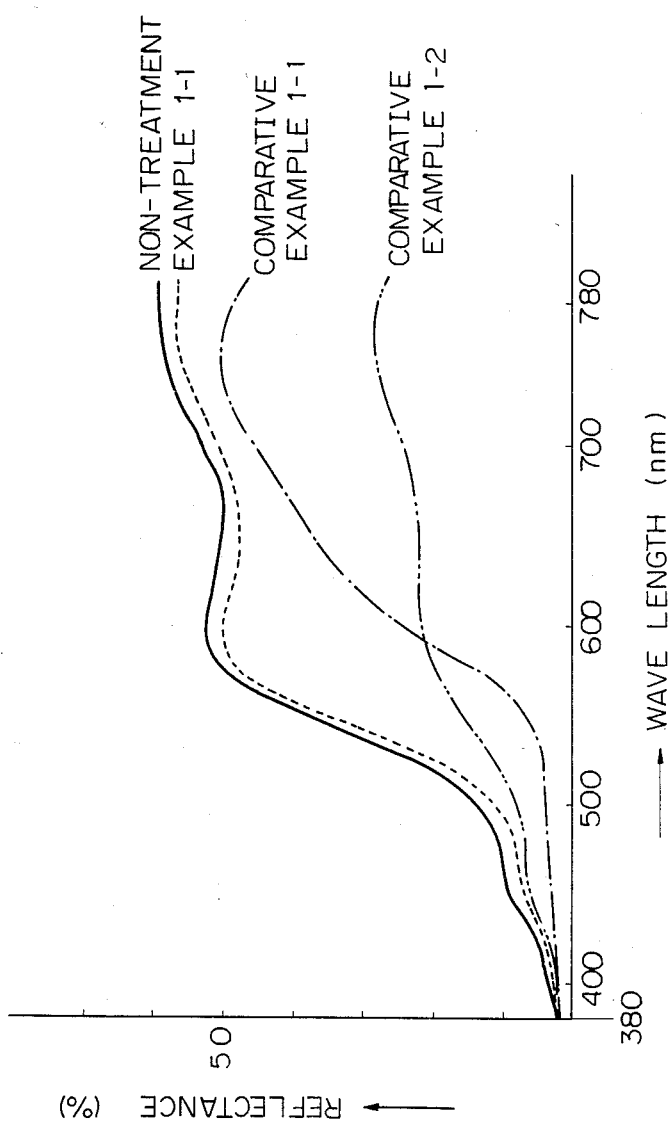
FIG. 1 shows the spectral curves of the yellow iron oxide powder samples of untreated powder Example 1-1, Comparative Example 1-1, and Comparative Example 1-2 measured by Hitachi Color Analyzer Model 607 in the range from 380 nm to 780 nm.

As mentioned above, when a powder is treated with, for example, a silicone oil, the use of heat, a catalyst, or a crushing force is required. This is because these techniques are based on the fact that the treating silicone oil is relatively inactive and that the powder to be treated has no activity.

However, many powders have surface activity and, due to the surface activity, co-existing substances such as perfumes, oils, and medicaments will be deteriorated. The present inventors have found an epoch-making method in which the polymerization of silicone is allowed to occur on the powder surface by utilizing the surface activity thereof to effect the desired modification of the surface simultaneously with a disappearance of the surface activity of the powder, thereby improving the properties of the powders.

Although there are no critical limitations to the powder materials to be modified according to the present invention, as long as the powders (or particulates) have some surface activities thereon, typical examples of such powders are inorganic pigments, metallic oxides and hydroxides, mica, organic pigments, pearlescent materials (or nacreous pigments), mineral silrcates, porous materials, carbons, metals, and composite powder or particulate materials, all having some active sites on the surface thereof. These powders may be used alone or in any mixture thereof. Furthermore, these powder materials can be treated by any conventional technique (e.g., alkali or acid washing, plasma treatment), prior to the modification according to the present invention. In the case of powder materials having many acid sites thereon (e.g., kaolinite, iron oxides, manganese violet), it is preferable to subject those powder materials to alkali washing, as the subsequent modification according to present invention results in a formation of the silicone polymer film having a network structure as described below. Furthermore, these powder materials to be modified may have other substances (e.g., coloring agents, medicaments, various additives) deposited thereon or included therein.

As mentioned above, according to the present invention, the silicone compound (I) in the form of a vapor can be brought into contact with the powder material having the active sites on the surface thereof at a temperature of 120° C. or less, preferably 100° C. or less in a closed chamber in such a manner that vaporized silicone compound (I) is deposited under a molecular state on the surface of the powder material, preferably under a pressure of 200 mmHg or less, more preferably 100 mmHg or less. Alternatively, the silicone compound (I) in the form of a vapor can be brought into contact with the powder material having the active sites on the surface thereof by feeding a gas mixture of the silicone compound (I) and a carrier gas at a temperature of 120° C. or less, preferably 100° C. or less.

The silicone compounds having the general formula (I) can be typically separated into two groups. That is, the first group of the silicon compounds (I) has the following structure (II):

$$(R^1HSiO)_a(R^2R^3SiO)_b \qquad (II)$$

wherein $R^1$, $R^2$, $R^3$, a and b are the same as defined above, and preferably $R^1$, $R^2$, and $R^3$ represent, independently, a lower alkyl group having 1 to 10 carbon atoms or an aryl group (e.g., a phenyl group) which may be substituted with at least one halogen atom and a+b is 3 to 7. Typical examples of such compounds are as follows:

(A)
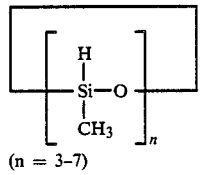
(n = 3-7)

(B)
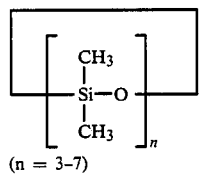
(n = 3-7)

(C)
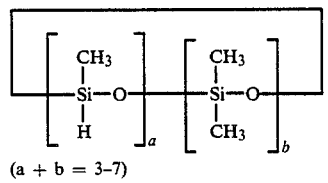
(a + b = 3-7)

These compounds (A), (B), and (C) may be used as above or in any mixture thereof.

The symbol n (or a+b) in the above-mentioned formulae preferably represents an integer of 3 to 7. As the number of n is smaller, the boiling temperature is lower, and the amount adsorbed through evaporation onto the powder is larger. Particularly, the trimer or tetramer is most suitable since it is readily polymerizable for steric properties. Also, the compound containing a hydrogen atom is highly reactive and suitable for the surface treatment. As for the treatment amount, this is not determined because the present invention is a vapor phase treatment and the cyclic organosiloxane evaporated will be polymerized by the active site of the powder after adsorption on the powder, and the time when the polymer has completely covered the active sites is the end point.

The second group of the silicone compounds (I) has the following structure (III):

$$(R^1HSiO)_a(R^2R^3SiO)_b(R^4R^5R^6SiO_{\frac{1}{2}})_c \quad (III)$$

wherein $R^1$, $R^2$, $R^3$, $R^5$, $R^6$, and a and b are the same as defined above and c is 2, preferably, $R^1$ to $R^6$ independently represent a lower alkyl group having 1 to 10 carbon atoms or an aryl group (e.g., a phenyl group), and a+b is preferably 2 to 5.

Typical examples of the compound (IV) are as follows:

(IV)
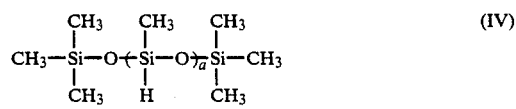

wherein a is 2 to 5.

The silicone polymer films coated on the surface of the powder materials typically have two types of structures. That is, when the polymerization is caused by a siloxane linkage (—Si—O—Si—), the resultant silicone polymer has a linear structure containing a —Si—O—Si— unit and preferably having a weight-average molecular weight of more than 200,000.

On the other hand, when the polymerization is caused by the dehydrogenation reaction of hydrosilyl linkages (Si-H) in the presence of a small or trace amount of $H_2O$ or $O_2$, the resultant silicone polymer has a net-work structure having a

unit derived from the polymerization of Si-H moieties as follows:

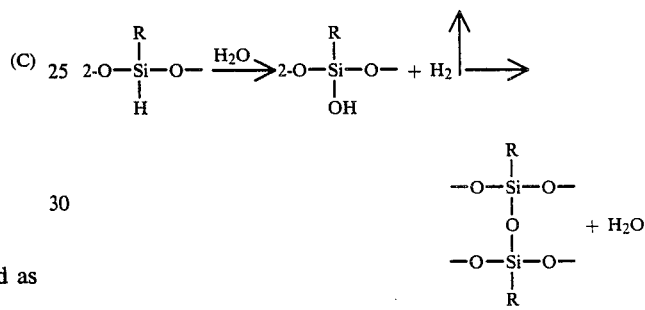

The preferable network polymer is such that 20% or more of the total Si atoms are converted into the above-mentioned unit

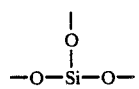

in the polymer film. The content of this unit can be determined from the IR absorbance of the methyl group in the polymer film.

The amount of the silicone compound (I) is not specifically determined, but the desired amount is specific in that the silicone compound is supplied in an amount which is necessary and sufficient to cover substantially the entire surface of the powders. Although the amount of the deposited polymer film may differ depending on the powder employed, generally speaking, the amount of the polymer film is 0.005% to 50% by weight based on the weight of the powder material.

Thus, in the present invention, any kind of powder can be treated without an excess or shortage of treatment. This is because the method of adding the treating agent is different from that of the prior art. In the present invention, the treating agent is not added in the form of a liquid but it is permitted to come into contact with the powder in molecular form and, therefore, the original treating agent may be either solid or liquid. Also, in view of the polymerization on the powder surface, a trimer is most readily polymerizable and, therefore, most suitable as a treating agent. That is, the specific feature of the present invention resides in the energy-saving type method in which the powder is left to stand in a low partial pressure state where an organosiloxane is volatilized at a temperature of 120° C. or lower, thereby permitting the vaporized product of the organosiloxane to be adsorbed, and deposited under the molecular state onto the powder, and polymerized from the active sites on the surface. This is entirely different from the method of the prior art in which a treating agent is sprayed and polymerized by heat.

According to the present invention, the silicone compound (I) is first deposited on the surface of the powder material and the polymerization thereof occurs due to the presence of active sites entirely prevailing on the surface of the powder materials. Thus, the uniform thin polymer film is formed. After forming the thin layer of the silicon polymer, no substantial polymerization occur thereover. Accordingly, the thickness of the silicone polymer film is generally 3 to 30 Å. On the other hand, when the thermal polymerization occurs, it is impossible to effect the thin layer- forming-polymerization. Furthermore, when the polymerization is effected in the presence of a catalyst, the polymerization occurs mainly around the catalyst and, therefore, it is not possible to uniformly cover or coat only the surface of the powder material.

The process for producing a modified powder of the present invention applies no heating treatment and, therefore, is applicable also for a pigment with low temperature stability. Thus, it can be utilized for a very wide scope of applications.

According to the basic embodiment of the present invention, the powder and the silicone compound may be placed in a closed chamber, and contained in separate vessels with their upper portions open. Due to the presence of polymerization activity, the silicone compound is polymerized on the powder material, whereby the partial pressure of the silicone compound on the powder surface is lowered and, therefore, the silicone compound in the vessel is then evaporated to be supplied to the powder material. Since the surface polymerization occurs in such an order, in this system the silicone compound is supplied only in a necessary amount without waste.

Since the process according to the invention is based on such a simple principle, special equipment is not necessarily required. For example, any closed or sealed chamber such as a desiccator or a constant temperature chamber may be used. The powder material may be agitated intermittently, in a chamber, so as to effect the desirable contact of the powder material with the vaporized silicone compound. It is also possible to employ an embodiment in which only the powder is previously placed in a closed chamber of 120° C. or less, preferably 100° C. or less, the silicone compound is volatilized under a predetermined partial pressure in another closed chamber of 120° C. or lower, and the volatilized silicone compound is introduced into the room in which the above powder is placed, through, for example, a pipe. Although there are no critical limitations to the pressure of the system, the polymerization is preferably carried out under a pressure of 200 mmHg or less, more preferably 100 mmHg or less. In any of the embodiments, the treatment time is from 30 minutes to 150 hours, and thereafter, the unpolymerized silicone compound is removed by degassing to obtain the desired product.

According to another embodiment of the present invention, the powder material can be treated by bringing it into contact with the silicone compound (I) in the form of a gas mixture thereof with a carrier gas. The silicone compound (I) can be mixed with a carrier gas by, for example, heating, if necessary, the silicone compound (I) until the vapor pressure thereof becomes 1 mmHg or more, preferably 100 mmHg or more, followed by introducing a carrier gas stream into the silicone compound (I) or the surface thereof. The feed rate of the carrier gas stream can be appropriately determined depending upon, for example, the vapor pressure of the silicone compound (I), the kinds and the amounts of the powder material, and the volume of the treating vessel, so that the treatment of the powder material can be completed for the predetermined time preferably 30 minutes to 150 hours. Examples of the carrier gases usable in the present invention are preferably inert gases such as nitrogen, argon, and helium, but air or a gas mixture of the above-mentioned inert gas with vaporized water, methanol or ethanol also may be used in the present invention.

According to the present invention, a gas mixture containing the silicone compound (I) is brought into contact with the powder material to be modified. The gas mixture contains the silicone compound (I) as a saturated vapor and, therefore, the contact temperature should be the same as or higher than the temperature of the gas mixture.

Thus, according to the present invention, an inert gas is simply introduced into a solution of the organosilicone compound and the molecules of the silicone compound are continuously adsorbed on the surface of the powder material, whereby the silicone compound is polymerized due to the presence of the active sites on the powder material. Thus, the method according to the present invention is an energy-saving type method and is completely different from the conventional spraying and thermal polymerizing methods.

Examples of the linear silicone compounds (III) are 1,1,1,2,3,4,4,4-octamethyltetrasiloxane, 1,1,1,2,3,4,5,5,5-nonamethylpentasiloxane, and 1,1,1,2,3,4,5,6,6,6-decamethyl hexasiloxane.

Examples of the cyclic silicone compounds (II) are dihydrogenhexamethyl cyclotetrasiloxane, trihydrogen pentamethyl cyclotetrasiloxane, tetrahydrogen tetramethyl cyclotetrasiloxane, dihydrogen octamethyl cyclopentasiloxane, trihydrogen heptamethyl cyclopentasiloxane, tetrahydrogen hexamethyl cyclopentasiloxane, and pentahydrogen pentamethyl cyclopentasiloxane. These compounds may be used alone or in any combination thereof.

As mentioned above, according to the present invention, various kinds of powder (or particulate) materials can be modified by coating the surfaces thereof with a silicone polymer film, as long as the powder materials have active sites on the surfaces thereof. Typical examples of such powder materials will now be explained below.

Inorganic pigment

Examples of the inorganic pigments capable of being modified according to the present invention are ultramarine blue, prussian blue, manganese violet, titanium-coated mica, bismuth oxycloride, iron oxides, iron hydroxide, titanium dioxide, titanium lower oxides, and chromium hydroxide. Of these pigments, ultramarine blue and prussian blue are typically modified according to the present invention.

As well-known in the art, ultramarine blue (i.e., sodium aluminum silicate containing sulfur) is generally represented by $Na_{6-9}Al_6Si_6O_{24}S_{2-4}$, and conventionally and widely used as a blue inorganic pigment in various fields (e.g., coating compositions, paints, inks, cosmetics, and detergents). Ultramarine blue has hydrophilicity and is stable up to a temperature of about 250° C. in an air atmosphere. However, ultramarine blue is not stable against an acid, although it is generally stable against an alkali. For example, ultramarine blue is gradually decomposed to generate hydrogen sulfide under an acidic condition (e.g., in the presence of a radical sulfate). As a result, the resultant ultramarine blue is discolored and becomes white. Obviously, the generation of hydrogen sulfide is especially not preferable in the fields of, for example, cosmetics. Furthermore, ultramarine blue is likely to generate hydrogen sulfide from a mechanical shearing force (e.g., grinding) or heating. Although various attempts have been made to obviate these disadvantages, as shown in Japanese Unexamined Patent Publication (Kokai) No. 54-95632 and Japanese Examined Patent Publication (Kokoku) No. 50-27483, the effects thereof are not sufficient from a practical point of view.

However, when ultramarine blue is modified with the silicone compound (I) according to the present invention, the generation of hydrogen sulfide under an acidic condition or at an elevated temperature or by a mechanical shearing force can be effectively prevented, and the decomposing action thereof against, for example, perfumes, can be suppressed. Thus, when the ultramarine blue modified with the silicone compound (I) is used under an acidic condition, no substantial deterioration occurs in aluminum or silver containers or in cosmetics. Furthermore, since the modified ultramarine blue is coated with the silicon polymer film, hydrophobicity is exhibited and the wettability is suppressed. Thus, the modified ultramarine blue can be formulated into an oil phase in an emulsion system.

The above-mentioned inherent disadvantages of ultramarine blue are believed to be caused by the presence of sulfur on the surfaces of ultramarine blue particles (i.e., surface sulfur). This surface sulfur is an active radical-type sulfur present on the surface of the crystalline lattice of ultramarine blue, which is likely to be susceptible to, for example, an acid, thermal, or mechanical shearing force action. However, according to the present invention, the surfaces of ultramarine blue particles are covered by the silicone polymer film to stabilize the ultramarine blue particles. Furthermore, since the silicone polymer film has a high transparency, there is no substantial difference between the unmodified and modified ultramarine blue particles. It should be noted that, due to the presence of the above-mentioned active sites on the surfaces of the ultramarine blue particles, the silicone compound (I) deposited on the surfaces thereof can be polymerized at a temperature of, for example, 120° C. or less, to form a silicone polymer film having a cross-linked network structure. Note, the temperature may be raised to 200° C. After coating the active surface with the silicone polymer film, further adsorption and polymerization do not occur.

Ultramarine blue to be modified according to the present invention can be any conventional ultramarine blue particles having a size of, for example, 0.1 to 20 μm. The amount of the silicone polymer present in the stabilized ultramarine blue powder particle is typically about 0.1% to 20% by weight, preferably 0.2% to 2.0% by weight based on the weight of the particle, depending upon the surface area and activity of the particle. The ultramarine blue particles may be dried prior to the treatment, if desired. Furthermore, conventional composite powder particles of, for example, plastics or metal oxides coated with ultramarine blue, also can be treated according to the present invention.

As well-known in the art, prussian blue (i.e., ferri ferocyanide) is generally represented by MFe (Fe $(CN)_6$), wherein M represents K, $NH_4$, or Na, and is conventionally and widely used as a blue inorganic pigment having a large coloring power in various fields (e.g., coating compositions, paints, cosmetics). However, prussian blue has a poor alkaline resistance although the acid resistance is strong. Furthermore, prussian blue is not strong against heating which causes the decomposition or a discoloration to dark brown. Further, upon heating, prussian blue is susceptible to reduction and tends to cause the deterioration of co-existence substances (e.g., perfumes).

However, when prussian blue is modified with the silicone compound (I) according to the present invention, the above-mentioned disadvantages of conventional prussian blue can be effectively eliminated. Thus, the modified prussian blue is formulated into compositions such as cosmetics, pharmaceutical compositions, and the stability thereof is remarkably improved because an undesirable interaction thereof with other ingredients (e.g., perfumes) can be eliminated. Furthermore, since the silicone polymer film is highly transparent, no substantial difference is observed in color between the unmodified and the modified prussian blue particles.

The prussian blue powder particles to be modified according to the present invention can be any conventional prussian blue powder particles, preferably having a size of 0.01 to 100 μm, more preferably 0.05 to 0.1 μm. The amount of silicone polymer coated on the surface of the modified prussian blue particles is typically 0.5% to 40% by weight, more preferably 5% to 30% by weight, depending upon the surface area of the particle.

Metal Oxide and Hydroxide

Examples of the metal oxides and hydroxides capable of being modified according to the present invention are magnesium oxide, magnesium hydroxide, calcium oxide, calcium hydroxides, aluminum oxide, aluminum hydroxide, silica, iron oxides ($\alpha$-$Fe_2O_3$, $\gamma$-$Fe_2O_3$, $Fe_3O_4$, FeO), iron hydroxides, titanium dioxide, titanium lower oxides, zirconium oxide, chromium oxides, chromium hydroxides, manganese oxides, cobalt oxides, nickel oxides, and zinc oxides. These oxides and hydroxides may be used alone or in any mixture thereof. Furthermore, composite oxides and composite hydroxides such as iron titanate, cobalt titanate, cobalt aluminate also can be used in the present invention. Composite materials comprising metal oxides or hydroxides coated on the core materials (e.g., titanium oxides coated mica, iron oxides coated nylon) can also be used in the present invention.

Although there are no critical limitations to the sizes of the metal oxide or hydroxide powder particles, metal oxides or hydroxides having a size of 0.001 to 200 μm, preferably 0.01 to 10 μm can be preferably coated with the silicone compound polymer film without causing agglomeration of the powder particles. The preferable coating amount of the silicone polymer is 0.1% to 20% by weight, more preferably 0.2% to 5.0% by weight, depending upon the kinds and surface area of the metal oxides or hydroxides.

As well-known in the art, metal oxides and hydroxides are conventionally and widely used as, for example, a colorant in various application fields (e.g., coating compositions, paints, cosmetics, inks) or as a magnetic material. However, conventional metal oxides and hydroxides generally have hydrophilicity and, therefore, have a poor dispersibility thereof in oils or organic solvents. Furthermore, metal oxides and hydroxides have catalyst activities and, therefore, deteriorate coexisting substances such as fats and oils and perfumes or cause discoloration due to the surface activities.

On the other hand, when metal oxides and hydroxides are modified with the silicone compounds (I) according to the present invention, the resultant metal oxides and hydroxides are uniformly covered with the silicone polymer film over the entire surfaces thereof and, therefore, the metal oxides and hydroxides are stabilized so that they do not interact with other agents and do not deteriorate perfumes and the like. Thus, when the modified metal oxides and hydroxides are formulated into various compositions (e.g., coating compositions, paints, cosmetics, pharmaceutical compositions), the stability thereof with the lapse of time is remarkably improved. Furthermore, since the silicone polymer film is very thin (e.g., 3 to 20Å) and is transparent, a color difference between the untreated and treated metal oxides and hydroxides is not observed and the magnetic properties of the metal oxides and hyroxides, if any, are not adversely affected. Thus, the modified $\gamma$-$Fe_2O_3$ or Co-$\gamma$-$Fe_2O_3$ may be advantageously used in the production of magnetic recording materials.

Mica

Examples of mica capable of being modified according to the present invention are muscovite, phlogopite, biotite, sericite, lepidolite, paragonite and artificial or synthetic mica having a fluorine atom substituted for the hydroxyl group of natural mica as well as baked or calcined products thereof. These mica may be used alone or in any mixture thereof.

Although raw mica ores may be modified according to the present invention, mica having a size of 0.5 to 40 $\mu$m may be preferably modified with the silicone compound (I) according to the present invention. However, mica can be modified according to the present invention after the cleaving thereof to a thin form (e.g., flakes). Although there are no critical limitations to the size of the mica, the preferable coating amount of the silicone polymer is 0.1% to 20% by weight, more preferably 0.2% to 5% by weight, in the case of the inherent mica. However, when the excess amount of the silicone compound (I) in the form of vapor is introduced, the mica is expanded due to the occurrence of the cleavage of the mica and, therefore, up to 20% to 90% by weight of the silicone polymer may be coated.

As well-known in the art, mica is conventionally and widely used as a filler or additive in, for example, coating compositions, inks, and cosmetics, as well as plastics and rubbers. However, mica generally has hydrophibicity and, therefore, has a poor dispersibility in oils and organic solvents. Furthermore, when mica is kneaded to plastics and rubbers, mica is likely to cause aggregation and uniform kneading is difficult.

On the other hand, when mica is modified with the silicone compound (I) according to the present invention, the modified mica is uniformly covered with the thin silicon polymer film over the entire surfaces thereof and, therefore, the mica is stabilized. Accordingly, when the modified mica is incorporated into compositions, the mica does not decompose or deteriorate co-existing substances (e.g., perfumes) and, therefore, the stability of the cosmetics and pharmaceutical compositions with the lapse of time is remarkably improved. Furthermore, since the silicone film is thin and transparent, there are no substantial differences in color between the untreated and modified mica. In addition, the modified mica exhibits hydrophobicity and can be formulated into an oil phase in the case of emulsions.

Organic Pigment

Examples of the organic pigments capable of being modified with the silicone compounds according to the present invention are C.I. 15850, C.I. 15850:1, C.I. 15585:1, C.I. 15630, C.I. 15880:1, C.I. 73360, C.I. 12085, C.I. 15865:2, C.I. 12075, C.I. 21110, C.I. 21095, and C.I. 11680, C.I. 74160 and zirconium, barium, or aluminum lakes of C.I. 45430, C.I. 45410, C.I. 45100, C.I. 17200, C.I. 45380, C.I. 45190, C.I. 14700, C.I. 15510, C.I. 19140, C.I. 15985, C.I. 45350, C.I. 47005, C.I. 42053, C.I. 42090.

The surfaces of these organic pigments may be treated with, for example, rosins. These organic pigments may be used alone or in any mixture thereof.

Although these are no critical limitations to the sizes of the organic pigments, the organic pigments having a size of 0.05 to 3.0 $\mu$m may be preferably coated or covered with the silicone polymer film. The preferable coating amount of the silicone polymer is 0.1% to 20% by weight, more preferably 0.2% to 5% by weight, depending upon the kinds and surface area of the organic pigments.

As well-known in the art, organic pigments are conventionally and widely used as a colorant in, for example, coating compositions, inks, and cosmetics, as well as plastics and rubbers. However, conventional organic pigments or the surface-treated products thereof cause the decomposition or deterioration of co-existing substances when formulated into compositions due to the interaction thereof, based on the presence of the active sites on the surface thereof, with the co-existing substances. Furthermore, certain organic pigments cause discoloration due to, for example, the absorption or desorption of the water of crystallization.

On the other hand, when organic pigments are modified with the silicone compound (I) according to the present invention, the modified organic pigments have the uniform silicone polymer film covering the entire surface thereof. Thus, the modified organic pigments become stable and have no interaction activities against the co-existing substances. Accordingly, when the modified organic pigments are formulated into compositions, the stability of the compositions with the lapse of time is remarkably improved. Furthermore, since the silicone polymer film is thin and highly transparent, there is no difference in the color of the organic pigments before and after the treatment. In addition, the dispersibility thereof in vehicles is also improved.

Pearlescent Pigment

Examples of pearlescent pigments (or nacreous pigments) are mica-titanium composite materials containing, as a titanium component, titanium dioxide, titanium lower oxides, titanium oxynitride, mica-iron oxide composite materials, bismuth oxychloride, and guanine. The mica-titanium composite materials may be mixed with colored pigments such as iron oxides, prussian blue, chromium oxide, carbon black, and carmine. These pearling pigments may be used alone or in any mixture thereof.

Although there are no critical limitations to the sizes of the pearlescent pigments, the pearlescent pigments having a size of 1 to 50 $\mu$m can be preferably coated or covered with the uniform silicone polymer film over the entire surface thereof. Note, in the case of the pearlescent pigments, the powder particles are preferably in the form of a flat shape (e.g., flakes). The preferable coating amount of the silicone powder is approximately 0.01% to 20% by weight.

As well-known in the art, pearlescent pigments are widely used in, for example, coating compositions, inks, cosmetics, plastics, ceramics, decorating, daily necessities, and fiber or textile products. Mica is generally formulated into these compositions, together with colored pigments, to exhibit various colored appearance. However, when mica composite materials are used together with other substances, the composite materials themselves are deteriorated or cause the discoloration or deterioration of co-existing substances.

On the other hand, according to the present invention, when the pearlescent pigments are uniformly coated or covered with the silicone polymer film, the resultant pearlescent pigments are stabilized and do not cause the deterioration or decomposition of co-existing substances.

Mineral Silicate

Examples of the mineral silicates capable of being modified according to the present invention are phyllosilicates and tectosilicates such as pyrophyllite, talc, chlorite, chrysotile, antigorite, lizardite, kaolinite, dickite, nacrite, halloysite, montmorillonite, nontronite, saponite, sauconite, and bentonite; natrolites such as natrolite, mesolite, scolecite, and thomsonite; heulandites such as heulandite, stilbite, epistibite; and zeolites such as analcite, harmotone, phillipsite, chabazite, and gmelinite. These silicate minerals may be used alone or in combination thereof. The phyllosilicates may have organic cations at the interface of the layers thereof or may be substituted with alkali metal or alkaline earth metal ions. The tectosilicates may include metallic ions in the fine pores thereof.

Although there are no critical limitations to the sizes of the silicate minerals, preferably silicate minerals having a size of 0.01 to 100 $\mu$m, more preferably 0.1 to 30 $\mu$m are modified with the silicone compound (I). The preferable coating amount of the silicone polymer is 0.1% to 20% by weight, more preferably 0.2% to 5.0% by weight, depending upon the kinds and surface area of the silicate mineral particles.

As well-known in the art, conventional silicate minerals optionally coated with certain silicone resins are widely used as an electric insulating material, filler, and additives in various fields (e.g., pharmaceutical compositions, ceramics, paper, rubbers, inks, cosmetics, and coating compositions). However, conventional silicate minerals unpreferably cause a deterioration of co-existing substances (e.g., perfumes, oils and fats, resins) when formulated into, for example, cosmetics and coating compositions.

On the other hand, according to the present invention, the silicate minerals can be stabilized because the surfaces of the silicate mineral particles can be uniformly coated or covered with a thin silicone polymer film. As a result, the modified silicate minerals do not deteriorate the co-existing substances when formulated therewith into compositions.

Porous Material

Examples of the porous materials capable of being modified with the silicone compound (I) according to the present invention are the above-mentioned silicate minerals; the above-mentioned mica; the above-mentioned metal oxides; $KAl_2(Al, Si_3)O_{10}F_2$, $KMg(Al, Si_3)O_{10}F_2$, and $K(Mg, Fe_3)(Al, Si_3)O_{10}F_2$; carbonate minerals such as $CaCO_3$, $MgCO_3$, $FeCO_3$, $MnCO_3$, $ZnCO_3$, $CaMg(CO_3)_2$, $Cu(OH)_2CO_3$, and $Cu_3(OH)_2(CO_3)_2$; sulfate minerals such as $BaSO_4$, $SrSO_4$, $PbSO_4$, $CaSO_4$, $CaSO_4.2H_2O$, $CaSO_4.5H_2O$, $Cu_4SO_4(OH)_6$, $KAl_3(OH)_6(SO_4)_2$, and $KFe_3(OH)_6(SO_4)_2$; phosphate minerals such as $YPO_4$, $(Ce, La)PO_4$ $Fe_3(PO_4)_2.8H_2O$, $Ca_5(PO_4)_3F$, $Ca_5(PO_4)_3Cl$, $Ca_5(PO_4)_3OH$, and $Ca_5(PO_4, CO_3OH)_3$ (F, OH); and metal nitrides such as titanium nitride, boron nitride, and chromium nitride. These materials may be used alone or in any mixture thereof. Furthermore these porous materials may be modified after granulation or molding, followed by baking or calcining. Furthermore, celluloses, fibers, and synthetic resins may be modified with the silicone compounds according to the present invention.

Although there are no critical limitations to the sizes of the porous materials, the porous materials having a size of 10 mm or less, more preferably 3 $\mu$m to 10 mm, may be preferably coated with the silicone polymer film. The preferable coating amount of the silicone polymer is approximately 0.01 to 20% by weight, depending upon the kinds and surface areas of the porous materials.

According to the present invention, the silicone compound deposited on the surface of the porous material is polymerized due to the presence of the active sites on the surface of the porous material and on the surface of the micropores of the porous material, whereby the entire surfaces of the porous material are coated with the silicone polymer in which the surface activity has disappeared. Thus, the modified porous materials do not cause a deterioration of substances such as pharmaceutical agents and perfumes. Accordingly, the modified porous materials may be advantageously used in, for example, perfumes, pharmaceutical compositions, toys, artificial organs, artificial bones, and ceramics.

Carbons

Examples of the carbons capable of being modified with the silicone compound (I) are the activated carbon and carbon black conventionally used in, for example, coating compositions, inks, tires, and cosmetics.

Although there are no critical limitations to the sizes of the carbon powder particles, preferably carbon powder particles having a size of 0.001 to 200 $\mu$m, more preferably 0.01 to 100 $\mu$m are modified with the silicone compounds according to the present invention. The preferable coating amount of the silicone polymer is approximately 0.1 to 50% by weight, more preferably 1% to 30% by weight, depending upon the kinds and surface areas of the carbon powder particles.

As well-known in the art, carbon powder particles are widely used as a colorant in, for example, coating compositions, inks, and cosmetics. However, since carbon is generally hydrophilic, the dispersibility thereof in oils and organic solvents is not good. Furthermore, carbon tends to deteriorate co-existing substances such as oil and fats and perfumes and to adsorb valuable agents thereon.

On the other hand, according to the present invention, the silicone compound deposited on the surface of the carbon powder particles is polymerized to form a uniform silicone polymer film on the entire surface thereof. As a result, the surface activity of the carbon disappears, and the modified carbon becomes hydrophobic or lyophillic. Accordingly, the modified carbon may be advantageously formulated into, for example, coating compositions, inks, and cosmetics, without causing any deterioration of co-existing substances such as oil and fats and perfumes.

Metals

Examples of the metals capable of being modified with the silicone compound (I) according to the present invention are iron, cobalt, nickel, copper, zinc, aluminum, chromium, tianium, zirconium, molybdenum, silver, indium, tin, antimony, tungsten, platinum, and gold, and the alloys thereof. When metals are coated with the silicone polymer film according to the present invention, the metals become stable (i.e., do not cause auto-oxidation upon contact with oxygen) and the dispersibility thereof is remarkably improved.

Accordingly, the modified metals can be advantageously used in, for example, magnetic recording materials.

Although there are no critical limitations to the sizes of the metals, the metals typically having a size of 0.01 μm to 5 mm may be preferably modified. The preferable coating amount of the silicone powder is approximately 0.01 to 20% by weight.

The modified powder or particulate materials according to present invention can be advantageously formulated as, for example, pigments, into any coating compositions including, for example, solvent-type, powder-type, emulsion-type, and aqueous-type coating compositions. Coating compositions generally contain resins, pigments, solvents, plasticizers, and other conventional additives as complicated multiple component mixtures. For example, pigments are formulated into coating composition (i) to provide, to the coating film, color; a hiding power; physical characteristics (e.g., hardness, strength, adhesiveness); and improved weather resistance; fluorescence, phosphorescence, magnetic properties, electric conductivity, and similar inherent characteristics of the pigments, (ii) to improve the flowability of the coating composition and the workability during coating, and (iii) to prevent the generation of rust, fungal growth, and injurious organisms. For these reasons, the compatibility of pigments with resins or dispersants has been studied. Pigments have various properties, for example, from hydrophilic properties to hydrophobic properties and cause color separation and other undersirable phenomena in the resultant coating compositions. When the modified pigments according to the present invention are formulated into coating compositions, the unpreferable color separation does not occur because the surfaces of the modified pigments are uniformly and entirely covered with the silicone polymer film. In addition, since the surface activities of the pigments are seal coated with the silicone polymer film, the deterioration of the coated film with the lapse of time can be effectively prevented. Furthermore, since the silicon polymer film coated on the surface of the modified pigment is very thin and transparent, the color of the modified pigment is not substantially changed when compared to the untreated pigment. Accordingly, color correction is not required after the modification. Typical examples of resin vehicles usable in the coating compositions according to the present invention are those conventionally used, such as, nitrocelluloses, oil modified alkyd resins, melamine resins, polyamide resins, epoxy resins, and unsaturated polyester resins.

The modified powder or particulate materials according to the present invention can be advantageously formulated as additives in cosmetic compositions. Typical examples of such additives are the abovementioned inorganic pigments, metallic oxides and hydroxides, mica, organic pigments, pearling pigments, mineral silicates, carbons, metals, and composite materials. When the unmodified powder materials are formulated into cosmetic compositions, perfumes contained in the cosmetic compositions are sometimes deteriorated or denatured due to the surface activities of these materials. As a result, the odor becomes worse. Contrary to this, when the modified powder materials according to the present invention are formulated into cosmetic compositions, these problems can be effectively solved since the surface activities are made to disappear by coating the entire surface of the powder materials with the silicone polymer film.

The modified powder materials according to the present invention can be formulated into any conventional cosmetic compositions including, for example, creams, liquid creams, packs, cosmetic powders, foundations, lipsticks, rouges, manicure preparation (e.g., nail polishes, nail enamels, enamel removers, nail treatments), eye cosmetics (e.g., eye liners, eye shadows), sunscreen preparations, deodorant preparations, shampoos, rinses, and hair treatments.

Any conventional cosmetic ingredients can be used, together with the modified powder materials. Typical examples of such ingredients are various hydrocarbons such as squalane, liquid paraffin, vaseline, microcrystalline wax, selecine, myristic acid, palmitic acid, stearic acid, oleic acid, isostearic acid, cetyl alcohol, hexadecyl alcohol, oleyl alcohol, cetyl-2-ethylhexanoate, 2-ethylhexyl palmitate, 2-octyldodecyl myristate, 2-octyldodecyl gum ester, neopentyl glycol-2-ethylhexanate, isooctyl triglyceride, 2-octyldodecyl oleate, isopropyl myristate isostearic acid triglycerides, coconut oil fatty acid triglyceride, olive oil, avacado oil, beeswax, myristyl myristate, mink oil, lanolin, and dimethyl polysiloxane; oils such as higher fatty acids, oils and fats, esters, higher alcohols, waxes, and silicone oils; organic solvents such as acetone, toluene, butyl acetate, and ethyl acetate; resins such as alkyd resins and urea resins; plasticizers such as camphor and acetyl tributyl citrate; UV absorbers; anti-oxidants; preservatives; surfactants; humectants; perfumes; water; alcohols; and thickening agents.

The treated powder prepared as described above has the following characteristics.

(1) Since a baking treatment is not applied but polymerization is carried out on the powder surface, the process is effective in energy saving and there is no change in color.

(2) Since a crushing force is not used, the process is effective in energy saving and there is no change or agglomeration of particles. There is also no color change caused by a crushing force.

(3) Treatment is simple and a superfluous treating agent is not used, and a uniform treatment can be effected by vapor phase treatment.

(4) Water repellency and blocking of the surface activity of the modified powder are substantially complete.

(5) According to the present invention, ultrafine power material, having a size of, for example, 0.005 to 0.05 μm can be advantageously coated with a uniform thin silicone polymer without causing unpreferable agglomeration.

EXAMPLE

The present invention will now be further illustrated by, but is by no means limited to, the following Examples and Comparative Examples, wherein all parts and percentages are on a weight basis unless otherwise specified.

EXAMPLE 1-1

In a desiccator, 10 g of yellow iron oxide contained in a 200 ml beaker and 5 g of tetramethyl tetrahydrogen cyclotetrasiloxane contained in a 20 ml sample tube were placed and allowed to stand at 50° C. After one day the treated powder was taken out of the desiccator and allowed to stand at 50° C. for 3 hours to give 10.185 g of the modified product.

COMPARATIVE EXAMPLE 1-1

To 10 g of yellow iron oxide was added 25 g of a hexane solution containing 0.185 g of tetramethyltetrahydrogen cyclotetrasiloxane, and after stirring well, the mixture was evaporated to dryness. Then, baking was carried out at 250° C., whereby the product became discolored to red.

COMPARATIVE EXAMPLE 1-2

A 10 g amount of yellow iron oxide and 0.019 g of calcium hydroxide were charged in a ball mill and mixed and ground for 30 minutes. Then, 0.185 g of hydrogen methyl polysiloxane (molecular weight=2600) was added, followed by mixing and grinding for 30 minutes. Next, 0.07 g of myristic acid was added and the mixture was ground for 30 minutes to give a treated product.

Each of the yellow iron oxides of Example 1-1, Comparative Example 1-1, Comparative Example 1-2, and the untreated sample was subjected to colorimetry, and measurements of water repellency, specific volume, and the behaviors of the decomposition of linalool were made by a microreactor.

Colorimetry

A sample was filled in a cell for measurement of the powder, and the measurement was conducted within the range of from 380 mn to 780 nm by a Hitachi Color Analyzer Model 607. The respective spectral curves are shown in FIG. 1. As apparently seen from the spectral curves, the untreated sample is considerably approximate to Example 1-1, and Comparative Example 1-1 and Comparative Example 1-2 have a different pattern. Also, the colorimetric results are represented in L, a and b, and the color difference ΔE calculated as shown in Table 1-1. It can be appreciated that the color difference ΔE of Example 1-1 is remarkably smaller than those of the Comparative Examples.

Water Repellency

A sample tube of 10 ml is charged with 5 ml of deionized water and with 0.1 g of powder and then subjected to shaking. The judgement was conducted as follows.

x ... dispersed in water.

Δ ... water repellent but partially dispersed in water.

o ... water repellent, and floated on the surface of the water.

The results are shown in Table 1-1. The untreated yellow iron oxide was well dispersed in water, Example 1-1 and Example 1-2 were water repellent and floated on the water, but Comparative Example 1-1 was partially dispersed in water due to incomplete treatment.

Specific Volume

A test tube for tapping specific volume was charged with 5 g of powder, and the specific volume was determined by repeating the tapping 200 times. The results are shown in Table 1-1.

It can be seen that Comparative Example 1-2 is agglomerated to a smaller specific volume by use of a ball mill. Also in Comparative Example 1-1, slight agglomeration occurred, and this may be considered to be due to evaporation of the solvent. In contrast, no agglomeration occurred in Example 1-1 due to vapor phase treatment, and the specific volume does not change from that prevailing before treatment.

TABLE 1-1

| | Color | | | Color difference | Water | Specific volume | Linalool decomposition |
| --- | --- | --- | --- | --- | --- | --- | --- |
| | L | a | b | ΔE | repellency | (ml/g) | activity |
| Yellow iron oxide (untreated) | 62.32 | 7.43 | 31.45 | — | x | 2.4 | Δ |
| Example 1-1 | 60.57 | 7.79 | 32.43 | 2.04 | o | 2.4 | o |
| Comparative Example 1-1 | 36.54 | 25.95 | 17.57 | 34.6 | Δ | 2.2 | x |
| Comparative Example 1-2 | 41.44 | 5.09 | 16.36 | 25.8 | o | 0.6 | x |

Decomposition of Linalool by Microreactor

In a Pyrex glass tube of 4 mm inner diameter, 20 mg of powder was fixed with quartz wool, and a decomposition measurement of linalool, which is a fragrant component, was carried out at a reaction temperature of 180° C. The amount of linalool injected was 0.3 μl, and nitrogen was used as the carrier gas at a flow rate of 50 ml/min.

Analysis was conducted by Shimazu GC-7A with the use of a column of 5 % FFAP/chromosorb w 80/100 of 3 mm×3 m at a column temperature of 80° C. (4 min-)–220° C. at a temperature elevation speed of 5° C./min.

Figure 2:
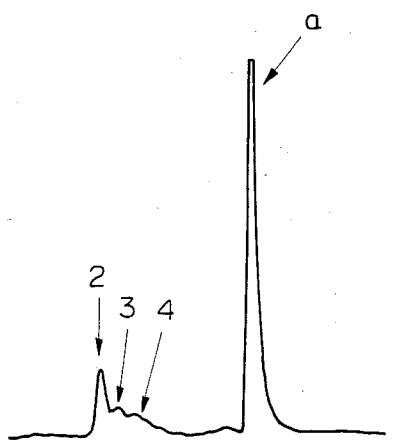
FIGS. 2 to 5 show gas chromatographic patterns of linalool decomposition of the yellow iron oxide powder samples of untreated powder, Example 1-1, Comparative Example 1-1, and Comparative Example 1-2, respectively, in which a indicates the peak of linalool and 1 to 6 indicate peaks of decomposed products, respectively.
Figure 3:
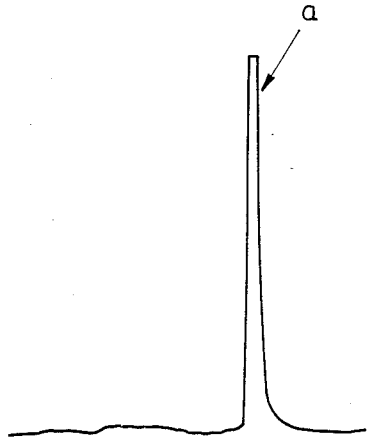
Figure 4:
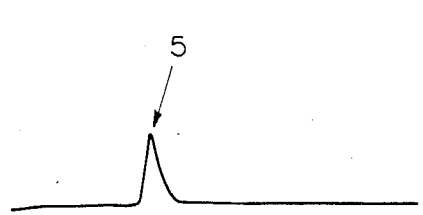

FIG. 2 shows the gas chromatographic pattern of linalool decomposition of the untreated yellow iron oxide, in which a is the peak of linalool, and 2, 3, and 4 are peaks of the decomposed products. FIG. 3 is the gas chromatographic pattern of linalool decomposition of Example 1-1. It can be seen that the decomposed products of 2, 3, 4 are reduced, indicating a loss of linalool decomposition activity. FIG. 4 is the linalool decomposition pattern of Comparative Example 1-1. There is no peak of linalool, but only the decomposed product 5. Thus, the powder of Comparative Example 1-1 has an increased decomposition activity, compared to the untreated powder, indicating a worsening of the perfume stability.

Figure 5:
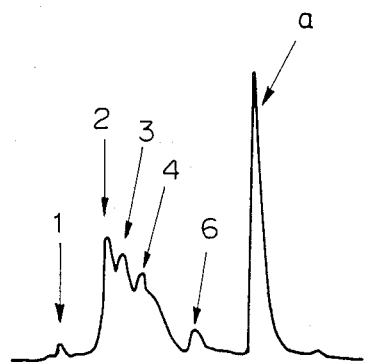

FIG. 5 is the linalool decomposition pattern of Comparative Example 1-2. As compared with the case of Comparative Example 1-1, the activity is weaker because of the remaining unreacted linalool, but the activity became stronger than that of the untreated powder.

As described above, Comparative Examples 1-1 and 2 have a strengthened linalool decomposition activity greater than the untreated powder, and a worsened perfume stability, while Example 1, has a weakened linalool decomposition activity and an improved perfume stability.

In the linalool decomposition activity shown in Table 1-1, untreated powder is shown by Δ, stronger activity than that of untreated powder by x, and weaker activity by o.

When the rssults in Table 1-1 are judged comprehensively, it can be seen that Example 1-1 has become water repellent with substantially the same color and specific volume as the untreated powder. Further, the perfume stability is improved, and it may be considered to be an excellent modified powder when formulated in cosmetics, etc.

EXAMPLE 1-2

In a gas sterilizer Kapokalizer CL-30B (Fuji Electric Co. Ltd.) 100 g of aluminum lake of C.I. 15985 and 50 g of trimethyl trihydrogen cyclotrisiloxane contained in separate vessels were placed and the inner pressure in the gas sterilizer was reduced to 100 mmHg by an aspirator, and the temperature was maintained at 30° C.

Six hours later, the inner pressure was returned to atmospheric by introducing air, followed by repeating the evacuation several times, to obtain 128 g of the modified powder. The modified powder exhibited a remarkable hydrophobicity and the linalool decomposing ability disappeared.

EXAMPLE 1-3

In a desiccator, 10 g of prussian blue and 10 g of tetramethyl tetrahydrogen cyclotetrasiloxane contained in separate vessels were left to stand at 100° C. for 6 hours. Then, after drying at 100° C. for 2 hours, 13.3 g of modified power was obtained. The modified powder exhibited a marked hydrophobicity and the linalool decomposing ability disappeared. Prussian blue was not decomposed, and there was no odor of cyan.

EXAMPLE 1-4

In a gas sterilizer Kapokalizer CL-30B (Fuji Electric Co. Ltd.), 10 g of zinc oxide and 5 g of hexamethyl cyclotrisiloxane contained in separate vessels were placed and the inner pressure was reduced to 300 mmHg, by an aspirator, and the temperature was maintained at 50° C.

After being left to stand overnight, the inner pressure was returned to atmospheric by introducing air, followed by evacuation for several times, to obtain 10.2 g of modified powder. The modified powder exhibited a marked hydrophobicity.

EXAMPLE 1-5

Into a rotary double cone type reactor of 100 liter volume (made of stainless steel, equipped with a lagging jacket) 20 kg of titanium dioxide was charged, and 400 g of tetramethyl tetrahydrogen cyclotetrasiloxane was charged into a stock liquor feeding tank (made of stainless steel, equipped with a lagging jacket) directly connected by a stainless steel pipe to the reactor, and the system was reduced by a vacuum pump to 100 mmHg. The temperature of the system was maintained at 90° C. by feeding a heating medium heated at 90° C. from the heating medium heating tank by a circulation pump to the lagging jackets of the reactor and the stock liquor feeding tank. The reactor was rotated three times after being left to stand for 10 minutes by means of a timer, to thereby mix and stir the titanium dioxide within the reactor, which operation was repeated for 10 hours. Then, the inner pressure was returned to atmospheric by the introduction of $N_2$ gas and 20.3 kg of the modified power was taken out. This was found to be entirely free from the agglomeration generally observed in untreated titanium dioxide, exhibited a good flow property and further, a marked hydrophobicity, with the linalool decomposing ability having disappeared.

EXAMPLE 2-1

In a 100 ml two-necked flask, 10.0 g of yellow iron oxide was charged as a powder material. One inlet of the flask was connected to a 30 ml bubbler and the other inlet was connected to a trap cooled with a dry ice in acetone. The flask and the bubbler were allowed to stand at 90° C. for 3 hours on a constant-temperature bath. Then, 5 g of tetramethyl tetrahydrogen cyclotetrasiloxane was charged as a treating agent into the bubbler. Nitrogen was fed to the bubbler at a flow rate of 4.0 ml/min for 15 hours. Thereafter, the connections between the flask and the bubbler and between the flask and the trap were separated and the flask was allowed to stand at 50° C. for 3 hours. Thus, 10.2 g of the modified product was obtained.

EXAMPLE 2-2

A 10.4 g amount of the modified powder material was obtained in the same manner as in Example 2-1 except that muscovite and 1,3,5-tris(3,3,3-trifluoropropyl)-1,3,5-trimethyl cyclosiloxane were used as the powder material and the treating agent, respectively.

The resultant modified powder exhibited excellent hydrophobicity with the linalool decomposing ability having disappeared.

EXAMPLE 2-3

Into a 100 liter rotary double cone type reactor (made of stainless steel, equipped with a lagging jacket), 20 kg of titanium dioxide was charged. The reactor was directly connected with a 10 liter treating agent feed vessel (made of stainless steel, equipped with a lagging jacket). A heating medium having a temperature of 90° C. was fed by a circulating pump to the jackets. A 1 liter amount of 1,3,5,7-tetramethyl cyclotetrasiloxane was added to the treating agent feed vessel and was then bubbled by introducing a nitrogen gas at a flow rate of 2 liters/min to the treating agent feed vessel. The reactor was provided with a condenser, where the unreacted treating agent was recovered while the nitrogen gas was discharged.

The reactor was rotated repeatedly for 1 minute at 10 minutes intervals, whereby the titanium dioxide was mixed within the reactor. This operation was repeated for 10 hours. Thus, 20.3 kg of the modified powder material was obtained. This was found to be entirely free from the agglomeration generally observed in the untreated titanium dioxide, exhibited a good flow property and further an excellent hydrophobicity, with the linalool decomposing ability having disappeared.

EXAMPLE 3-1

A 100 g amount of ultramarine blue powder and 20 g of tetrahydrogen tetramethyl cyclotetrasiloxane were separately charged into separated vessels, which were connected to each other in a closed relationship. The system was allowed to stand at room temperature for 96 hours. After 96 hours, 100.78 g of the treated ultramarine blue powder was obtained and was further allowed to stand at 50° C. for 24 hours in a dryer. Thus, 100.32 g of the finally treated ultramarine blue was obtained.

EXAMPLE 3-2

A 10 g amount of ultramarine blue powder and a mixed liquid of 1 g of tetrahydrogen tetramethyl cyclotetrasiloxane and 1 g of pentahydrogen pentamethyl cyclopentasiloxane were separately charged into separate vessels, which were connected to each other in a closed relationship. The system was allowed to stand at 90° C. for 24 hours. Then, the treated ultramarine blue was recovered and was allowed to stand at 90° for further 24 hours in a dryer. Thus, 10.13 g of the finally modified ultramarine blue powder was obtained.

The modified ultramarine blue powder obtained above was evaluated with respect to (i) the polymer structure, (ii) the chloroform, dissolution matter of the silicone polymer, (iii) the generation of hydrogen sulfide determined by a hydrogen sulfide detection method, (iv) the generation of hydrogen sulfide determined by silver plate blackening, (v) the linalool decomposition activity, and (vi) water repellency as follows.

(i) Crosslinking Ratio of Coated Silicone Polymer Film.

The value 100 a/(a+b) in the silicone polymer (RSiO$_3$)$_a$(RHSiO)$_b$ represents the crosslinking ratio(%) of the SiH group.

A 100 mg amount of a sample and 900 mg of KBr powder were uniformly mixed and the mixture was placed in a cell for measuring diffusion reflection spectrum. Thus, the spectrum was determined by means of a Fourier transformation infrared spectrophotometer under the following conditions:
Resolving power: 1 cm$^{-1}$
Integrating number: 100 (times)
Wavenumber range: 1300–1200 cm$^{-1}$ The resultant spectrum was subjected to Kubelka-Munk function transformation by the attached computer software, followed by peak division according to a deconvolution method.

After the peak dividing, the spectrum showed peaks at 1261 cm$^{-1}$ and 1272 cm$^{-1}$. The peak at 1261 cm$^{-1}$ belonged to the methyl group of the unit (RHSiO)$_b$ and the peak at 1272 cm$^{-1}$ belonged to the unit (RSiO$_{3/2}$)$_a$. Thus, the crosslinking ratio of the silicone polymer was determined from the following calculating equation:

$$\text{Crosslinking ratio} = \frac{ⓐ}{ⓐ + ⓑ} \times 100$$

wherein  ⓐ : peak height at 1271 cm$^{-1}$
ⓑ : peak height at 1261 cm$^{-1}$ wherein
ⓐ : peak height at 1272 cm$^{-1}$
ⓑ : peak height at 1261 cm$^{-1}$ (ii) Chloroform Soluble Matter A 1–100 g amount of a sample was dispersed in 100–1000 ml of chloroform and, after filtration, the filtrate was concentrated in an evaporator. Then, the molecular weight was determined by means of gel permeation chromatography. The apparatus used was a Japan Analytical Industry Co., Ltd. LC-08 provided with three columns of B4H, B3H, and B3H.

The solvent used was chloroform (1.07 ml/min) and RI was used as a detector. The molecular weight was estimated from a calculation curve of standard polystyrene.

The ultramarine blue after the filtration was dried at 80° C. for 24 hours and used in the determination of the water repellency.

(iii) Determination of H$_2$S by H$_2$S Determination Method

A 200 ml three-necked round bottom flask with a magnetic stirrer was equipped with a 50 ml dropping funnel and a simple type gas detector, which was then connected to a tap aspirator so that the generated hydrogen sulfide gas was evacuated at a constant pressure. The hydrogen sulfide could be directly read from the graduation of 0.1% to 2.0%.

The determination was carried out by using this apparatus as follows. That is, 0.5 g of the ultramarine blue was charged into the three-necked round bottom flask and was uniformly dispersed in 5 ml of deionized water. Then, 5 ml of 1N HCl was added through the funnel at one time, followed by stirring with the magnetic stirrer. The ultramarine blue was decomposed by the acid and the amount of the generated hydrogen sulfide(%) was read directly from the graduation.

(iv) Determination of H$_2$S by Silver Plate Blackening Test Method

The ultramarine blue sample and a silver plate were placed in a closed vessel at 80° C. for 2 days. The blackening degree of the silver plate was visually observed.

(v) Decomposition of Linalool by Microreactor

In the same manner as in the Example 1-1

(vi) Water Repellency

In the same manner as in the Example 1-1 The results are as follows.

| Ex. No. | 100a/(a + b) | Chloroform soluble | H$_2$S detection | Ag plate blackening | Linalool stability | Water repellency |
| --- | --- | --- | --- | --- | --- | --- |
| Example | 44% | No*[1] | No | No change*[2] | Excellent*[3] | Good |

| Ex. No. | 100a/(a + b) | Chloroform soluble | H₂S detection | Ag plate blackening | Linalool stability | Water repellency |
|---|---|---|---|---|---|---|
| 3-1 | | | | | | |
| Example 3-2 | 73% | No | No | No change | Excellent | Good |

*¹M.W. > 200,000
*²1.0% for 10 minutes in the case of untreated ultramarine blue.
*³Decomposition occurred in the case of untreated ultramarine blue.

EXAMPLE 3-3

A 100 g amount of potassium prussian blue and 50 g of tetrahydrogen tetramethyl cyclotetrasiloxane were separately charged into separate vessels, which were connected to each other in a closed system. The system was allowed to stand at 80° C. for 72 hours in a desiccator. Then, the prussian blue was taken out from the desiccator to obtain 132.3 g of the treated prussian blue. The resultant prussian blue was allowed to stand at 80° C. for a further 24 hours in a dryer. Thus, 130.1 g of the modified prussian blue was obtained.

EXAMPLE 3-4

A 100 g amount of ammonium prussian blue and 50 g pentamethyl cyclotetrasiloxane were separately charged into separate vessels, which were connected to each other in a closed system. The system was allowed to stand at 50° C. for 72 hours to obtain 125.3 g of the treated prussian blue. The treated prussian blue was allowed to stand at 80° C. for further 24 hours in a dryer. Thus, 124.3 g of the modified prussian blue was obtained.

The evaluation results are as follows.

| Example No. | 100a/(a + b) | Chloroform soluble | Water repellency | Linalool stability |
|---|---|---|---|---|
| Example 3-3 | 61% | No | Good | Good |
| Example 3-4 | 57% | No | Good | Good |

EXAMPLE 3-5

A 5 kg amount of potassium prussian blue was charged into a 100 liter rotary double cone type reactor (made of stainless steel, equipped with a lagging jacket) and 500 g of a silicone compound having the following structure:

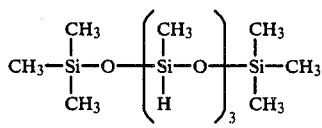

was charged into a stock liquor feeding tank (made of stainless steel, equipped with a lagging jacket) directly connected to the reactor by a stainless steel pipe. The system was evacuated to 20 mmHg by a vacuum pump. The temperature of the system was maintained at 90° C. by feeding a heating medium heated at 90° C. from the heating medium heating tank by a circulation pump to the lagging jackets of the reactor and the stock liquor feeding tank. The reactor was rotated three times after being allowed to stand for 10 minutes, by means of a timer, thereby to mix and stir the prussian blue within the reactor, which operation was repeated for 10 hours. Then, the inner pressure was returned to atmospheric by introduction of N₂ gas and 6.4 kg of the modified prussian blue was obtained.

The evaluation results of the modified prussian blue was as follows:

(i) Crosslinking ratio: 64%

(ii) Chloroform soluble matter: No soluble matter was obtained. Thus, the molecular weight was more than 200,000

(iii) Water repellency: Water repellent, and floated on the surface of water (iv) Linalool stability: Linalool was only slightly decomposed, whereas the untreated powder remarkably decomposed linalool.

EXAMPLE 3-6

A 5 kg amount of ultramarine blue powder was charged into a 100 liter rotary double cone type reactor (made of stainless steel, equipped with a lagging jacket) and 500 g of a silicone compound having the following structure:

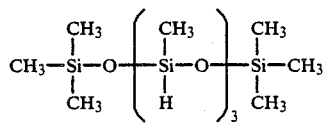

was charged into a stock liquor feeding tank (made of stainless steel, equipped with a lagging jacket) directly connected to the reactor by a stainless steel pipe. The system was evacuated to 20 mmHg by a vacuum pump. The temperature of the system was maintained at 90° C. by feeding a heating medium heated at 90° C. from the heating medium heating tank by a circulation pump to the lagging jackets of the reactor and the stock liquor feeding tank. The reactor was rotated three times after being allowed to stand for 10 minutes, by means of a timer, thereby to mix and stir the ultramarine blue within the reactor, which operation was repeated for 5 hours. Then, the inner pressure was returned to atmospheric by introducting N₂ gas and 5.3 kg of the modified ultramarine blue was obtained.

The resultant modified powder had similar properties as mentioned above.

EXAMPLE 4-1

A 100 g of amount of finely divided titanium dioxide powder (0.025 μm) and 20 g of tetrahydrogen tetramethyl cyclotetracyloxane were separately charged into separate vessels, which were connected to each other in a sealed system, followed by allowing to stand at room temperature for 96 hours. Thus, 107.85 g of the treated finely divided titanium dioxide powder was obtained. The resultant powder was then allowed to stand at 50° C. for a further 24 hours in a dryer.

As a result, 104.80 g of the modified finely divided titanium dioxide powder was obtained.

EXAMPLE 4-2

A 100 g amount of red iron oxide powder and 20 g of dihydrogenhexamethyl cyclotetrasiloxane were separately charged into separate vessels, which were connected to each other in a sealed system, followed by allowing to stand at 80° C. for 72 hours. Thus, 101.50 g of the treated red iron oxide was obtained. The resultant powder was then allowed to stand at 100° C. for a further 24 hours in a dryer.

As a result, 100.60 g of the modified red iron oxide powder was obtained.

EXAMPLE 4-3

A 10 g amount of zinc oxide (or zinc white) powder and 2 g of pentahydrogen pentamethyl cyclopentasiloxane were separately charged into separate vessels, which were connected to each other in a sealed system, followed by allowing to stand at 90° C. for 12 hours. Thus, 10.90 g of the treated zinc oxide powder was obtained. The resultant powder was then allowed to stand at 90° C. for a further 24 hours in a dryer.

As a result, 10.60 g of the modified zinc oxide powder was obtained.

EXAMPLE 4-4

A 10 g amount of zirconium oxide powder and 2 g of tetrahydrogen tetramethyl cyclotetrasiloxane were separately charged into separate vessels, which were connected to each other in a sealed system, followed by allowing to stand at 30° C. for 24 hours. Thus, 11.60 g of the treated zirconium oxide was obtained. The resultant powder was then allowed to stand at 90° C. for a further 24 hours in a dryer.

As a result, 10.80 g of the modified zirconium oxide was obtained.

EXAMPLE 4-5

A 5 kg amount of finely divided titanium dioxide was charged into a 100 liter rotary double cone type reactor (made of stainless steel, equipped with a lagging jacket) and 500 g of a silicone compound having the following structure:

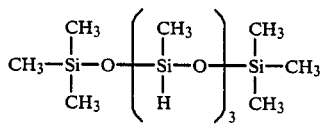

was charged into a stock liquor feeding tank (made of stainless steel, equipped with a lagging jacket) directly connected to the reactor by a stainless steel pipe. The system was evacuated to 20 mmHg by a vacuum pump. The temperature of the system was maintained at 90° C. by feeding a heating medium heated at 90° C. from the heating medium heating tank by a circulation pump to the lagging jackets of the reactor and the stock liquor feeding tank. The reactor was rotated three times after being allowed to stand for 10 minutes, by means of a timer, thereby to mix and stir the titanium dioxide within the reactor, which operation was repeated for 10 hours. Then, the inner pressure was returned to atmospheric by introducting $N_2$ gas and 5.3 kg of the modified powder was obtained.

The modified powder obtained above were evaluated with respect to various tests as follows. The results are shown in Table 4 below.

(i) Coating Condition

The uniform coating conditions of the silicone polymer film coated on the surface of powder according to the present invention can be determined by means of an X-ray photoelectron spectroscopic analyzer (i.e., Shimazu ESCA 750). The determination was carried out under the conditions of 12 kW and 30 mA in the analyzer provided with an Mg conical anode, a semicircular filament, and a 2 $\mu$ aluminum filter.

The sample was adhered to a both-surface adhesive type tape and the measurement was carried out within the range of 0 to 760 eV.

The coverage of the silicone polymer film can be confirmed because the coated silicone polymer exhibits bonding energies of $Si_{2S}$ and $Si_{2P}$ tracks different from the untreated powder.

(ii) Crosslinking Ratio

See above

(iii) Chloroform Soluble Matter

See above

(iv) Water Repellency

See above

(v) Linalool Stability

See above

(vi) Colorimetry

See above

(vii) Specific Volume

See above

(viii) Chemical Agent Stability

The color deterioration to dark brown of vitamin E, resorcinol, or γ-oryzanol was tested by directly bringing the sample powder to the chemical agent. The results are evaluated as follows:

x : Changed to dark brown
Δ: Slightly changed to yellow
x : No change

TABLE 4

| No. | Coating Condition | Cross-linking Ratio | Chloroform Soluble-matter | Water Repellency | Linalool Stability | Chemical Agent*1 Stability (1) | (2) | (3) |
|---|---|---|---|---|---|---|---|---|
| Example 4-1 | — | 52 | No | ○ | ○ | ○ | ○ | ○ |
| Untreated | — | — | — | x | Δ | x | x | ○ |
| Example 4-2 | — | 81 | No | ○ | ○ | — | — | — |
| Untreated | — | — | — | x | Δ | — | — | — |
| Example 4-3 | — | 40 | No | ○ | ○ | ○ | ○ | ○ |
| Untreated | — | — | — | x | Δ | ○ | ○ | x |
| Example 4-4 | — | 23 | No | ○ | ○ | ○ | ○ | ○ |

TABLE 4-continued

Figure 6:
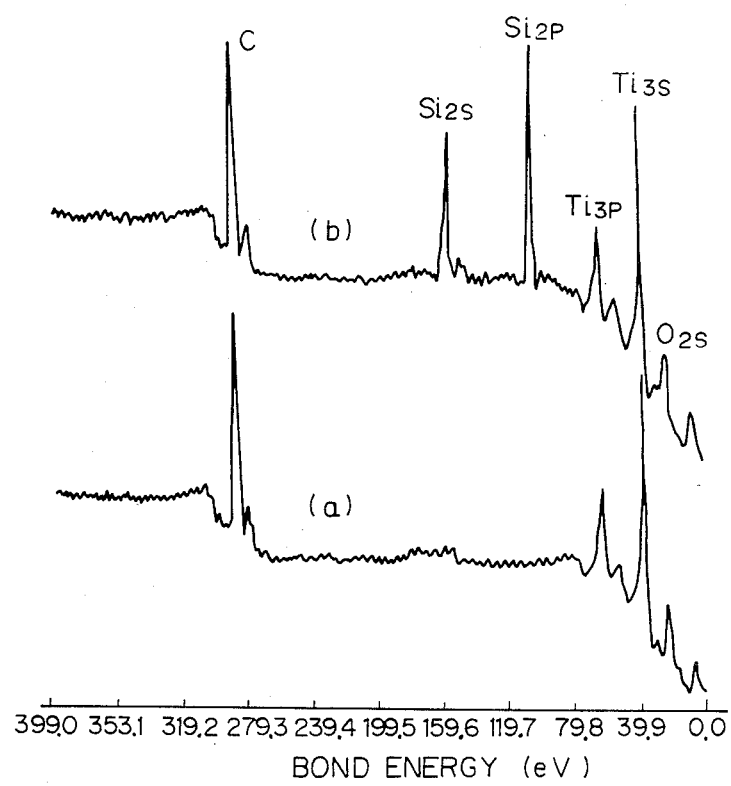
FIG. 6 shows the X-ray photoelectron spectrum of the titanium dioxide powder samples of the untreated powder (i.e. chart (a)) and Example 4-5 (i.e., chart (b))

| No. | Coating Condition | Cross-linking Ratio | Chloroform Soluble-matter | Water Repellency | Linalool Stability | Chemical Agent*1 (1) | (2) | (3) |
| --- | --- | --- | --- | --- | --- | --- | --- | --- |
| Untreated | — | — | — | x | Δ | O | O | O |
| Example 4-5 | See FIG. 6 | 66*2 | No | O | O | O | O | — |
| Untreated | — | — | — | x | Δ | x | x | — |

Figure 7:
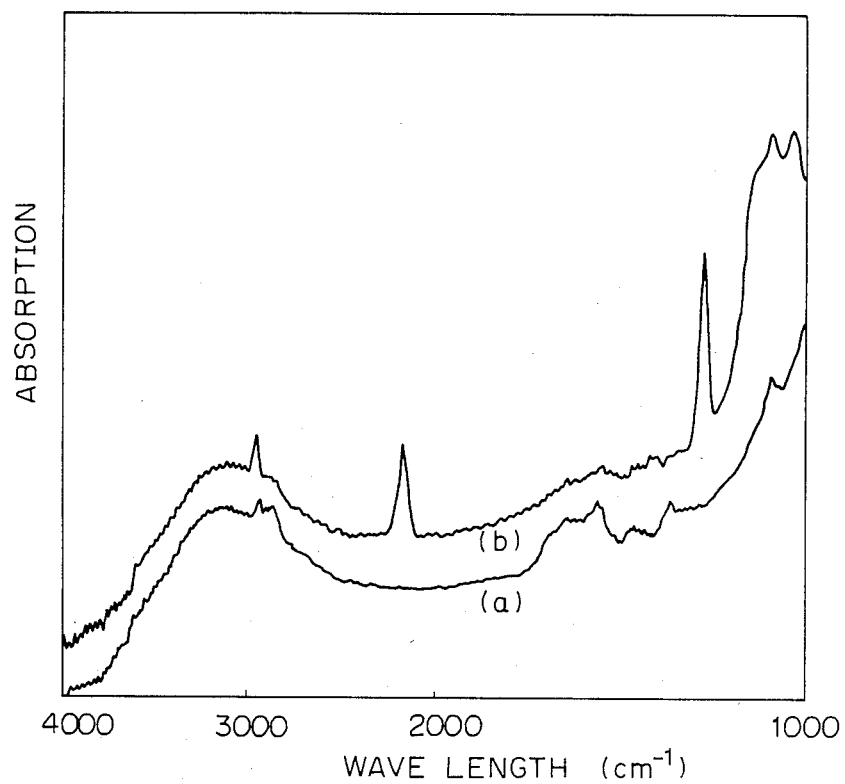
FIG. 7 shows the IR-absorption spectrum of the titanium dioxide powder samples of the untreated powder (i.e., chart (a)) and Example 4-5 (i.e., chart (b))

*1(1) . . . Vitamin E, (2) . . . γ-oryzanol, (3) . . . resorcinol
*2See FIG. 7

EXAMPLE 4-6

A 10 kg amount of spherical composite powder comprising 65 parts of nylon powder (5 μm) coated with 35 parts of titanium dioxide (0.2 μ) was charged into a 100 liter rotary double cone type reactor (made of stainless steel, equipped with a lagging jacket) and 1 kg of a silicone compound having the following structure:

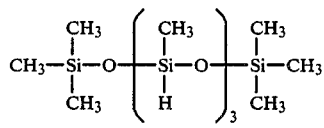

was charged into a stock liquor feed tank (made of stainless steel, equipped with a lagging jacket) directly connected to the reactor by a stainless steel pipe. N₂ was charged into the reactor by bubbling it from the bottom of the feed tank. The temperature of the system was maintained at 70° C. by feeding a heating medium heated at 70° C. from the heating medium heating tank by a circulation pump to the lagging jackets of the reactor and the stock liquor feeding tank. The reactor was rotated three times after being allowed to stand for 10 minutes by means of a timer thereby to mix and stir the composite powder within the reactor, which operation was repeated for 7 hours. Then, the silicone compound was removed and only N₂ was introduced to the reactor while rotating for a further 2 hours. After the temperature was cooled to room temperature, 10.4 kg of the modified powder was recovered.

The modified powder exhibited remarkable water repellency, without losing the good flow property specific to the starting composite powder, and did not cause the unpreferable brown discoloration of vitamin E and γ-oryzanol, which was caused by the starting composite powder.

EXAMPLE 5-1

A 20 g amount of muscovite having an average particle size of 2 μm and 2 g of tetrahydrogen tetramethyl cyclotetrasiloxane were separately charged into separate vessels, which were connected to each other in a sealed system, followed by allowing to stand at 80° C. for 16 hours. Thus, 21.8 g of the treated muscovite was obtained. The resultant powder was then allowed to stand at 100° C. for a further 24 hours in a dryer.

As a result, 21.4 g of the modified muscovite was obtained.

COMPARATIVE EXAMPLE 5-1

A 2 g amount of octamethyl cyclotetrasiloxane was added to 20 g of muscovite having an average particle size of 2 μm, followed by stirring with a small sized stirrer. Then, the mixture was baked in an electric oven for 2 hours at 250° C.

COMPARATIVE EXAMPLE 5-2

A 20 g amount of muscovite having an average particle size of 2 μm and 1.4 g of hydrogen methyl polysiloxane having an average molecular weight of 3000 were charged into a ball mill, followed by milling for 30 minutes.

EXAMPLE 5-2

A 100 g amount of biotite and 1 g of dihydrogen hexamethyl cyclotetrasiloxane were separately charged into separate vessels and were then placed in a closed container, followed by allowing to stand at 80° C. for 72 hours. The resultant powder was dried at 100° C. in a dryer.

As a result, 100.6 g of the modified biotite was obtained.

EXAMPLE 5-3

A 100 g amount of synthetic mica having an average particle size of 8 μm and 5 g of a mixed solution of tetrahydrogen tetramethyl cyclotetrasiloxane and pentahydrogen pentamethyl cyclopentasiloxane were separately charged into a a gas sterilizer. The inside atmosphere was then evacuated to 100 mmHg by an aspirator and the temperature was maintained at 30° C. After 6 hours, air was fed into return the inside pressure to a normal pressure. The inside atmosphere was evacuated several times. Thus, 103.2 g of the modified synthetic mica was obtained.

EXAMPLE 5-4

Figure 8:
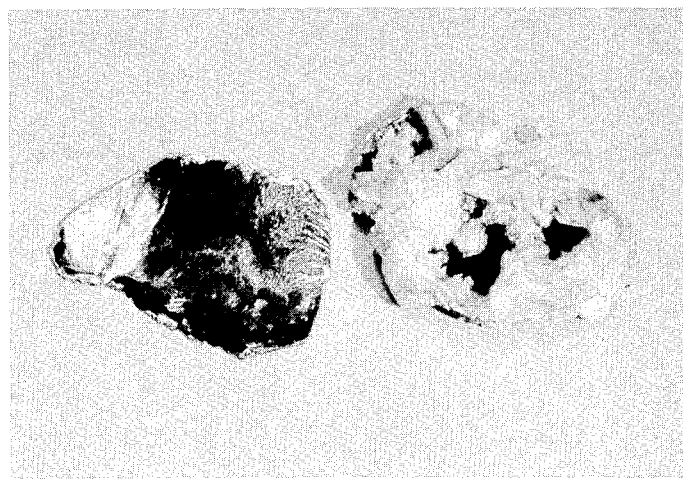
FIGS. 8 and 9 are photographs showing the changing conditions of the starting mica ore and the modified stable mica obtained by coating the mica ore with a silicone polymer film in Examples 5-4 and 5-5, respectively, according to the present invention.

A raw ore of biotite and 10 g of tetrahydrogen tetramethyl cyclotetrasiloxane were allowed to stand at 50° C. for 24 hours in a desiccator. Thus, the surface of biotite was cleaved, expanded, and whitened, as shown in FIG. 8. As is clear from FIG. 8, the thinner cleavage was effected when the mica was brought into contact with the vaporized silicone compound.

EXAMPLE 5-5

Figure 9:
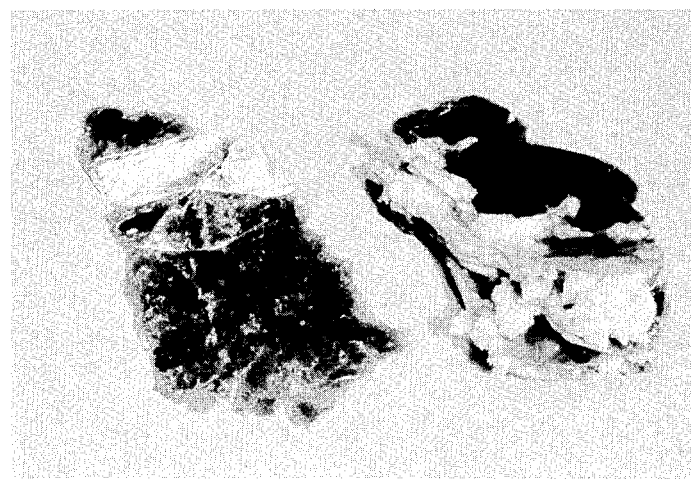

A raw ore of phologopite and 10 g of pentahydrogen pentamethyl cyclopentasiloxane were allowed to stand at 80° C. for 24 hours in a desiccator. Thus, the surface of phlogopite was cleaved, expanded, and whitened, as shown in FIG. 9.

The modified powder obtained above were evaluated with respect to various tests in the same manner as mentioned above. The results are shown in Table 5 below.

TABLE 5

| No. | Crosslinking ratio (%) | Water repellency | Linalool stability |
| --- | --- | --- | --- |
| Example 5-1 | 45 | O | O |

TABLE 5-continued

| No. | Crosslinking ratio (%) | Water repellency | Linalool stability |
|---|---|---|---|
| Comparative Example | | | |
| 5-1 | — | x | x |
| 5-2 | — | Δ | Δ |
| Untreated mica | — | x | Δ |

EXAMPLE 5-6

A 5 kg amount of muscovite having an average diameter of 2 μm was charged into a 100 liter rotary double cone type reactor (made of stainless steel, equipped with a lagging jacket) and 500 g of a silicone compound having the following structure:

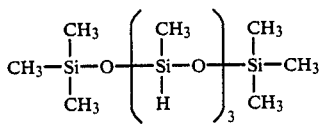

was charged into a stock liquor feeding tank (made of stainless steel, equipped with a lagging jacket) directly connected to the reactor by a stainless steel pipe. The system was evacuated to 20 mmHg by a vacuum pump. The temperature of the system was maintained at 90° C. by feeding a heating medium heated at 90° C. from the heating medium heating tank by a circulation pump to the lagging jackets of the reactor and the stock liquor feeding tank. The reactor was rotated three times after being allowed to stand for 10 minutes by means of a timer thereby to mix and stir the muscovite within the reactor, which operation was repeated for 5 hours. Then, the inner pressure was returned to atmospheric by introduction of $N_2$ gas and 5.3 kg of the modified muscovite was obtained.

The modified muscovite obtained above was evaluated with respect to various tests as mentioned above. The results are as follows.

(i) Crosslinking Ratio 100a/(a +b): 70%

(ii) Structure of Silicone Polymer

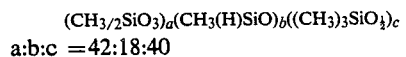
a:b:c =42:18:40

(iii) Chloroform Soluble Matter No soluble matter was found (i.e., M.W.>200,000).

(iv) Water Repellency and Linalool Stability

| Sample | Water Repellency | Linalool Stability |
|---|---|---|
| Untreated Muscovite | x | Δ |
| Example 5-6 | O | O |

EXAMPLE 5-7

A 10 kg amount of synthetic mica obtained by substituting the OH group of muscovite with fluorine was charged into a 100 liter rotary double cone type reactor (made of stainless steel, equipped with a lagging jacket) and 10 kg of a silicone compound having the following structure:

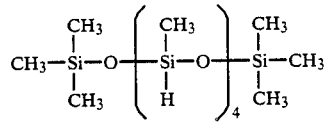

was charged into a stock liquor feeding tank (made of stainless steel, equipped with a lagging jacket) directly connected to the reactor by a stainless steel pipe. $N_2$ was charged through the feeding tank by bubbling $N_2$ into the tank. The temperature of the system was maintained at 70° C. by feeding a heating medium heated at 70° C. from the heating medium heating tank by a circulation pump to the lagging jackets of the reactor and the stock liquor feeding tank. The reactor was rotated three times after being allowed to stand for 10 minutes by means of a timer, and thereafter, the silicone compound was removed and $N_2$ was introduced into the reactor, which operation was continued for 12 hours. Then, the temperature was returned to room temperature. Thus, 19.6 kg of the modified mica was obtained.

The resultant modified product was fluffy and exhibited remarkable water repellency. Furthermore, the linalool decomposition activity thereof had disappeared and, therefore, the stability of the perfume contained, together with the modified mica in the conposition was remarkably improved.

EXAMPLE 6-1

A 1000 g amount of β-type C.I. 15850:1 (lithol rubine BCA) powder and 100 g of tetrahydrogen tetramethyl cyclotetrasiloxane were separately charged into separate vessels, which were then placed in a desiccator at 80° C. for 16 hours. The treated powder was then allowed to stand at 90° C. for a further 24 hours in a dryer.

As a result, 1043 g of the modified C.I. 15850:1 (lithol rubine BCA) powder was obtained.

The resultant powder and the untreated powder were evaluated in the same manner as mentioned above. The results are as follows:

(i) Chloroform Soluble Matter

A 82 mg amount (i.e., 1.9% of the total silicone compound) of the silicone polymer was dissolved in chloroform from 100 g of modified C.I. 15850:1 (lithol rubine BCA). The average molecular weight of the dissolved polymer was about 8000.

(ii) α- and β-Transformation

The β-type C.I. 15850:1 (lithol rubine BCA) was transformed to the α-type in the presence of water. The percentage of the α-type of the modified powder was determined according to the X-ray peak thereof according to the following equation:

$$\alpha\text{-type transformation \%} = \frac{h\alpha}{h\alpha + h\beta} \times 100$$

wherein
hα . . . height at 2θ=20.75°
hβ . . . height at 2θ=21.60°
The results are as follows:

| Sample | α-transformation % | | | | |
|---|---|---|---|---|---|
| | 1 day | 3 days | 6 days | 10 days | 20 days |
| Untreated powder | 20 | 94 | 100 | 100 | 100 |
| Modified powder | 0 | 0 | 0 | 3 | 18 |

As clear from the above results, the delay of the α-transformation in the modified powder exhibits the difficulty of the transmission of water due to the formation of the silicone polymer film entirely covering the powder particles.

EXAMPLE 6-2

A 300 g amount of C.I. 15850:1 (lithol rubine BCA) (β-type crystalline) powder and 100 g of the silicone having the following structure:

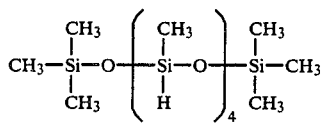

were separately charged into separate vessels and were then allowed to stand at 80° C. for 16 hours in a desiccator. After recovering from the vessel, the treated powder was dried at 90° C. for 24 hours in a dryer. Thus, 311 g of the modified powder was obtained.

The resultant powder and the untreated powder were evaluated in the same manner as mentioned above.

The results are as follows:

(i) Chloroform Soluble Matter

A 230 mg amount (i.e., about 6.3% of the silicone polymer) of the silicone polymer having an average molecular weight of about 4500 was dissolved in chloroform.

(ii) α- and β-type transformation

| Sample | α-transformation % | | | | |
|---|---|---|---|---|---|
| | 1 day | 3 days | 6 days | 10 days | 20 days |
| Untreated powder | 20 | 94 | 100 | 100 | 100 |
| Modified powder | 0 | 0 | 14 | 31 | 65 |

As is clear from the results above, the transformation of the β-type to the α-type was delayed. It is clear that, since the powder was entirely covered with the silicone polymer film, it becomes difficult to transmit water through the silicone polymer film.

(iii) Bleeding Property

Since the C.I. 15850:1 (lithol rubine BCA) is a calcium lake pigment, it is dissolved to some extent in water when dispersing therein. Accordingly, the bleeding property of the powder was evaluated.

A 0.5 g amount of C.I. 15850:1 (lithol rubine BCA) was dispersed in 100 ml of deionized water and was allowed to stand at room temperature for one day. The amount of the dissolved C.I. 15850:1 (lithol rubine BCA) was determined, after filtration, by the absorbance at a maximum absorption wavelength of 490 mm by using a 1 cm cell.

The results are as follows:

| Sample No. | Absorbance |
|---|---|
| Untreated powder | 0.15 |
| Modified powder | 0.04 |

As is clear from the results shown above, according to the present invention, the bleeding property of the powder was sustained due to the formation of uniform silicone polymer film entirely covering the powder.

EXAMPLE 7-1

A 20 g amount of mica-titanium pearling material having an average particle size of 25 μm and 2 g of the silicone compound having the following structure:

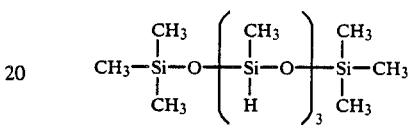

were separately charged into separate vessels, followed by allowing to stand at 80° C. for 24 hours in a desiccator. Then, the resultant mica-titanium pearling material was taken out of the vessel and was further allowed to stand at 100° C. for 24 hours.

As a result, 21.2 g of the modified pearling agent was obtained.

EXAMPLE 7-2

A 20 kg amount of mica-iron oxide type pearling agent was charged into a 100 liter rotary double cone type reactor (made of stainless steel, equipped with a lagging jacket) and 400 g of the silicone compound having the following structure:

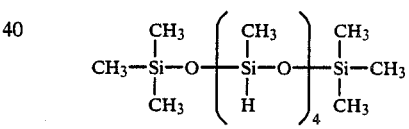

was charged into a stock liquor feeding tank (made of stainless steel, equipped with a lagging jacket) directly connected to the reactor by a stainless steel pipe. The inside atmosphere was evacuated to 20 mmHg by a vacuum pump. The temperature of the system was maintained at 90° C. by feeding a heating medium heated at 90° C. from the heating medium heating tank by a circulation pump to the lagging jackets of the reactor and the stock liquor feeding tank. The reactor was rotated three times after being allowed to stand for 10 minutes by means of a timer thereby to mix and stir the mica-iron oxide within the reactor, which operation was repeated for 10 hours. Then, the inner pressure was returned to atmospheric by introducting N₂ gas and 20.36 kg of the modified powder was obtained.

The resultant modified powder and the unreacted sample were evaluated in the same manner as mentioned above. The results are shown below.

| Sample No. | Crosslinking Ratio 100a/(a + b) | Water Repellency | Linalool Stability |
|---|---|---|---|
| Unreacted powder | — | x | Δ |

| Sample No. | Crosslinking Ratio 100a/(a + b) | Water Repellency | Linalool Stability |
|---|---|---|---|
| Example 7-1 | 74 | O | O |
| Example 7-2 | 62 | O | O |

EXAMPLE 7-3

A 20 g amount of titanium-mica pearling material having an average particle size of 25 μm and 2 g of tetrahydrogen tetramethyl cyclotetrasiloxane were separately charged into separate vessels and were then allowed to stand at 80° C. for 12 hours in a desiccator. The treated pearling material was recovered and was then allowed to stand at 100° C. for 24 hours in a dryer.

As a result, 20.8 g of the modified titanium-mica pearling material was obtained. The modified powder material thus obtained had similar properties to those mentioned above.

EXAMPLE 8-1

A 100 g amount of kaolinite having an average particle size of 5 μm and 20 g of tetrahydrogen tetramethyl cyclotetrasiloxane were separately charged into separate vessels and were then allowed to stand at 80° C. for 12 hours in a desiccator. The treated kaolinite was recovered and was further allowed to stand at 100° C. for 24 hours in a dryer.

As a result, 102.6 g of the modified kaolinite was obtained.

EXAMPLE 8-2

A 20 kg amount of talc was charged into a 100 liter rotary double cone type reactor (made of stainless steel, equipped with a lagging jacket) and 400 g of tetrahydrogen tetramethyl cyclotetrasiloxane was charged into a stock liquor feeding tank (made of stainless steel, equipped with a lagging jacket) directly connected to the reactor by a stainless steel pipe. The temperature of the system was maintained at 90° C. by feeding a heating medium heated at 90° C. from the heating medium heating tank by a circulation pump to the lagging jackets of the reactor and the stock liquor feeding tank. The reactor was rotated three times after being allowed to stand for 10 minutes, by means of a timer, thereby to mix and stir the treated talc within the reactor, which operation was repeated for 10 hours. Then, the inner pressure was returned to atmospheric by introduction of N₂ gas and 20.3 kg of the modified talc was obtained.

EXAMPLE 8-3

A 5 kg amount of montmorillonite powder was charged into a 100 liter rotary double cone type reactor (made of stainless steel, equipped with a lagging jacket) and 500 g of trihydropentamethyl cyclotetra siloxane was charged into a stock liquor feeding tank (made of stainless steel, equipped with a lagging jacket) directly connected to the reactor by a stainless steel pipe. N₂ was fed to the reactor by bubbling it through the liquor feeding tank. The temperature of the system was maintained at 70° C. by feeding a heating medium heated at 70° C. from the heating medium heatng tank by a circulation pump to the lagging jackets of the reactor and the stock liquor feeding tank. The reactor was rotated three times after being allowed to stand for 10 minutes by means of a timer, which operation was repeated for 7 hours. Then, the silicone compound was removed and, while N₂ was fed to the reactor, the system was heated to 100° C. The rotation was continued for further 2 hours to remove the silicone monomer from the system. The temperature was cooled to room temperature and the modified montmorillonite powder was obtained.

EXAMPLE 8-4

A 50 g amount of organically modified montmorillonite powder (i.e., Benton 38 available from N.L. Co.) and 50 g of tetrahydrogen tetramethyl cyclotetrasiloxane were separately charged into vessels and were then allowed to stand at 50° C. for 48 hours in a vacuum type low-temperature dryer DPF-31 (manufactured by Yamato Kagaku K.K.). Thereafter, the powder was further allowed to stand at 80° C. Thus, 85 g of the modified powder was obtained, which was expanded when compared with the state before the treatment.

The resultant modified powder and the starting untreated powder were evaluated in the same manner as mentioned above.

The results are as follows.

TABLE

| No. | Crosslinking Ratio | Chloroform Soluble-Matter | Water Repellency | Linalool Stability |
|---|---|---|---|---|
| Example 8-1 | 35 | No | O | O |
| Untreated | — | — | x | Δ |
| Example 8-2 | 42 | — | O | O |
| Untreated | — | — | Δ | Δ |
| Example 8-3 | 32 | — | O | O |
| Untreated | — | — | x | Δ |
| Example 8-4 | 62 | — | O | O |
| Untreated | — | — | Δ | Δ |

EXAMPLE 8-5

A 100 g amount of kaolinite having an average particle size of 5 μm and 20 g of 1,1,1,2,3,4,4,4-octamethyl tetrasiloxane were separately charged into separate vessels, followed by allowing them to stand at 80° C. for 24 hours in a desiccator. The resultant kaolinite was then allowed to stand at 100° C. for 24 hours in a dryer. Thus, 103.4 g of the modified kaolinite was obtained.

The resultant modified kaolinite had properties similar to those mentioned above.

EXAMPLE 9-1

A 100 g amount of spherical porous silica having a specific surface area of 350 m²/g, a micropore size of 116 Å, and a particle size of 10 μm and 100 g of tetramethyl tetrahydrogen cyclotetrasiloxane were separately charged into separate vessels, followed by allowing to stand at 80° C. for 24 hours in a desiccator. The resultnat silica was then allowed to stand at 100° C. for 2 hours in a dryer. Thus, 123.3 g of the modified silica was obtained.

COMPARATIVE EXAMPLE 9-1

A 10 g amount of tetramethyl tetrahydrogen cyclotetrasiloxane was added to 10 g of the porous silica used in Example 9-1, followed by allowing them to react at 80° C. for 24 hours in a closed system.

COMPARATIVE EXAMPLE 9-2

A 10 g amount of the porous silica used in Example 9-1 and 20 g of alumina ball were charged into a ball mill. After agitating for 30 minutes, 10 g of tetramethyl tetrahydrogen cyclotetrasiloxane was added and the mixture was then agitated for one hour.

The modified or treated porous silica obtained above was evaluated as follows:

(i) Change of Shape

The modified silica obtained in Example 9-1 maintained the original spherical shape and good flowability. No agglomeration was observed. Contrary to this, the treated silica in Comparative Example 9-1 caused agglomeration to become solid or mass, although the original spherical shape was maintained. Furthermore, in Comparative Example 9-2, the original shape was not maintained at all and the mixture became a slurry in which the silica and the resin were solidified as a mixture.

(ii) Change of Micropore Size

The micropore size was determined by means of an Autosorb-1 manufactured by Quantachrome Co., Ltd.

In Example 9-1, the diameter of the micropore of the porous silica was changed from 116 Å to 102 Å. Thus, the size of the micropore was reduced by 7 Å in radius. This means that a thin silicone polymer film having a thickness of about 7 Å was uniformly coated in the inside surface of the micropore.

Contrary to this, in Comparative Examples 1 and 2, the micropores substantially disappeared because the liquid silicone compounds entered into the micropores and, therefore, the coating only on the surface of the micropore was impossible.

(iii) Surface Activity

The surface activity of the silica was evaluated from the decomposition of linalool, a compound of perfumes or fragrants, in a microreactor as mentioned above.

The untreated silica decomposed linalool to form myrcene, limonene, cis-ocimene, trans-ocinene, and the like. This illustrates that solid acids are present on the surface of the untreated silica and cause the dehydration of the tertiary alcohol of linalool.

Contrary to this, the modified silica obtained in Example 9-1 did not decompose the linalool at all. This clearly illustrates that the surface activity on the surface of the silica had disappeared due to the coverage of the thin silicone polymer film. Although no evaluations were carried out of the products of Comparative Example 9-1 and 9-2, it is believed that the active sites on the surface were sufficiently covered by the silicone oligomer.

EXAMPLE 9-2

A 100 g amount of alumina (a particle size of 3 mm$\phi$, a specific surface area of 2 m$^2$/g, baked at 1100° C. after granulation) and 100 g of tetramethyl tetrahydrogen cyclotetrasiloxane were separately charged into separate vessels, followed by allowing to stand at 25° C. in a desiccator for 72 hours. The alumina was taken out from the desiccator and was further allowed to stand at 50° C. for 3 hours.

As a result, 100.6 g of the modified alumina was obtained. The modified alumina exhibited remarkable hydrophobicity and the linalool decomposition activity had disappeared as in Example 9-1.

EXAMPLE 9-3

A 50 g amount of hollow type silica (particle size 3 $\mu$, specific density 0.23, and specific surface area 412 m$^2$/g) and 20 g of pentamethyl trihydrogen cyclotetrasiloxane were separately charged into separate vessels, followed by allowing to stand at 80° C. for 24 hours in a desiccator. After taking out from the desiccator, the silica was further allowed to stand at 50° C. for 3 hours. Thus, 66.4 g of the modified silica was obtained.

The modified silica obtained above exhibited remarkable hydrophobicity and the linalool decomposition activity had disappeared.

EXAMPLE 9-4

A doll having a weight of 53.5 g and obtained by molding clay (mainly containing kaolin) and baking it at 1000° C. and 10 g of tetramethyl tetrahydrogen cyclotetrasiloxane were separately charged into separate vessels, followed by allowing to stand at 50° C. for 24 hours. After taking out from the desiccator, the doll was further allowed to stand at 50° C. for 3 hours. The weight of the treated doll was 56.2 g.

The resultant doll exhibited remarkable hydrophobicity. The doll was allowed to stand at 20° C. for 12 hours, together with a commercially available rose type perfume preparation, and then the doll was left in a closed glass container at 40° C. for 30 days. The perfume stability was excellent when compared to the untreated doll.

EXAMPLE 10-1

A 100 g amount of carbon black powder and 50 g of tetrahydrogen tetramethyl cyclotetrasiloxane were separately charged into separate vessels and were allowed to stand at room temperature for 96 hours in a closed container. Thus, 126.50 g of the treated carbon black powder was obtained. The treated carbon black was further allowed to stand at 50° C. for 24 hours in a dryer.

As a result, 120.3 g of the modified carbon black was obtained.

The modified carbon black was evaluated in the same manner as mentioned above.

The results are as follows:

| Sample | Crosslinking Ratio 100a/(a + b) | Water Repellency | Linalool Stability |
|---|---|---|---|
| Untreated Carbon | — | X | Δ |
| Example 10-1 | 70 | O | O |

EXAMPLE 11-1

The following ingredients were throughly mixed in a ball mill in the following ratios. Thus, a coating composition was obtained.

| Ingredient | Part |
|---|---|
| Powder material obtained in Example 3-1 | 100 |
| Vinyl chloride-vinyl acetate copolymer | 10 |
| Polyurethane resin | 20 |
| Toluene | 100 |
| Methyl ethyl ketone | 100 |

COMPARATIVE EXAMPLE 11-1

The coating composition was prepared in the same manner as in Example 11-1, except that the powder material was not used. When the coating compositions obtained in Example 11-1 and Comparative Example 11-1 were coated on a polyester film in a conventional manner. When the coated films were visually evaluated, the coating composition of Example 11-1 exhibited deep color and good gloss when compared to that of Comparative Example 11-1, due to the good dispersibility.

EXAMPLE 12-1

Preparation of Pressed Powder

The pressed powder having the following composition was prepared by using the modified powder materials according to the present invention.

|     | Ingredient | Part |
| --- | --- | --- |
| (1) | Modified muscovite of Example 5-6 | 30 |
| (2) | Modified talc of Example 8-2 | 65.8 |
| (3) | Iron oxide pigment | 0.1 |
| (4) | Squalane | 2.0 |
| (5) | 2-Ethylhexyl palmitate | 2.0 |
| (6) | Perfume | 0.1 |

The ingredients (1), (2), and (3) were mixed in a Henschel mixer, followed by spraying a heated mixture of the ingredients (4), (5), and (6), the mixture was then ground and molded in a container. Thus, the desire pressed powder was obtained.

COMPARATIVE EXAMPLE 12-1

The pressed powder was prepared in the same manner as in Example 12-1, except that the untreated mica and talc were used instead of the modified mica and talc.

The pressed powde compositions obtained in Example 12-1 and Comparative Example 12-1 were evaluated. The results are as follows:

| No. | Extendability | Cosmetic finish retainability | Water repellency | Odor stability |
| --- | --- | --- | --- | --- |
| Example 12-1 | ⊚ | ⊚ | ⊚ | ⊚ |
| Comparative Example 12-1 | Δ | Δ | xx | x |

⊚ . . Excellent
O . . Good
. . . Fair
x . . . Poor
xx . . . Bad

EXAMPLE 12-2

Preparation of Foundations. A foundation having the following composition was prepared.

|     | Ingredient | Parts |
| --- | --- | --- |
| (1) | Mixture of modified powder materials* | 78 |
| (2) | 2-Ethylhexyl palmitate | 5.5 |
| (3) | Liquid paraffin | 5.0 |
| (4) | Sorbitan sesquioleate | 1.0 |
| (5) | Preservative | 0.3 |
| (6) | Perfume | 0.2 |

*A mixture of five kinds of modified powder materials, each prepared in the same manner as in Example 2-3, i.e., 10 parts of titanium dioxide, 10 parts of muscovite, 35 parts of sericite, 20 parts of talc, and 3 parts of iron oxide. In this connection, a similar mixture of modified powder materials may be prepared by using a mixture of powder materials which have not been modified, and treating that mixture in the same manner as in Example 2-3.
A heated mixture of the ingredients (2), (3), (4), (5), and (6) was added to the ingredient (1), followed by mixing and grinding. The resultant composition was packed in a container. Thus, the desired foundation capable of being used either with or without water was obtained.

COMPARATIVE EXAMPLE 12-2

The foundation was prepared in the same manner as in Example 12-2 except that the modified powder was replaced by metallic soap.

The evaluation results are as follows:

| No. | Extendability | Cosmetic finish retainability | Water repellency |
| --- | --- | --- | --- |
| Example 12-2 | ⊚ | ⊚ | ⊚ |
| Comparative Example 12-2 | O | O | X |

⊚ . . . Excellent
O . . Good
. . . Fair
X . . . Poor

EXAMPLE 12-3

Preparation of Powder Eye Shadow

The eye shadow having the following composition was prepared.

|     | Ingredient | Parts |
| --- | --- | --- |
| (1) | Modified talc of Example 8-2 | 20 |
| (2) | Modified pearling pigment of Example 7-2 | 18.5 |
| (3) | Modified ultramarine blue of Example 3-1 | 50 |
| (4) | Modified iron oxide of Example 4-2 | 4.0 |
| (5) | Squalane | 4.0 |
| (6) | Cetyl 2-ethyl hexanoate | 2.0 |
| (7) | Sorbitan sesquioleate | 1.0 |
| (8) | Preservative | 0.3 |
| (9) | Perfume | 0.2 |

The ingredients (1) to (4) were mixed in a Henschel mixer and a heated mixture solution of the ingredients (5) to (9) was sprayed thereto. The resultant mixture was ground and then packed in a container. Thus, the desired eye shadow was obtained.

COMPARATIVE EXAMPLE 12-3

The eye shadow was prepared in the same manner as in Example 12-3, except that the modified talc, pearling agent, and iron oxide were replaced by the unmodified powders, respectively.

COMPARATIVE EXAMPLE 12-4

The eye shadow was prepared in the same manner as in Example 12-2, except that the modified powders of Example 12-2, were replaced by the unmodified powders.

The evaluation results are as follows.

| No. | Extendability | Cosmetic finish retainability | Water repellency | Odor stability |
| --- | --- | --- | --- | --- |
| Example 12-3 | O | ⊚ | ⊚ | ⊚ |
| Comparative Example 12-3 | Δ | x | x | O |
| Comparative Example 12-4 | Δ | x | xx | x |

⊚ . . . Excellent
O . . Good
Δ . . . Fair
x . . . Poor
xx . . . Bad

EXAMPLE 12-4

Preparation of Nail Enamel

The nail enamel having the following composition was prepared as follows:

|  | Ingredient | Part |
|---|---|---|
| (1) | Nitrocellulose | 12 |
| (2) | Modified alkyd resin | 12 |
| (3) | Acetyltributyl citrate | 5 |
| (4) | Butyl acetate | 38.4 |
| (5) | Ethyl acetate | 6 |
| (6) | n-Butyl alcohol | 2 |
| (7) | Toluene | 21 |
| (8) | Modified red iron oxide of Example 2-1 | 0.5 |
| (9) | Modified titanium dioxide of Example 4-1 | 0.1 |
| (10) | Pearling pigment | 2 |
| (11) | Organically modified Montmorillonite | 1 |

The ingredients (1) to (3) and (5) to (7) and a portion of the ingredient (4) were dissolved and a gelled mixture of the component (11) and the remainder of the component (4) was added, followed by adding the ingredients (8) to (10). The resultant mixture was packed in a container to obtain the desired nail enamel.

COMPARATIVE EXAMPLE 12-5

The nail enamel was prepared in the same manner as in Example 12-4, except that modified powders of Example 12-4 were replaced by the untreated powders.

The nail enamel of Example 12-4 was superior to that of Comparative Example 12-5 in the dispersion stability of the pigments and the adherence of the content to the container.

EXAMPLE 12-5

UV Preventive Stick

The UV light preventive stick having the following composition was prepared as follows:

|  | Ingredient | Part |
|---|---|---|
| (1) | Modified titanium dioxide of Example 4-1 | 20 |
| (2) | Talc | 10 |
| (3) | Mica | 11 |
| (4) | Iron oxide | 0.5 |
| (5) | Carnauba wax | 1 |
| (6) | Solid paraffin | 3 |
| (7) | Liquid paraffin | 45 |
| (8) | Isopropyl myristate | 8 |
| (9) | Sorbitan sesquioleate | 1.5 |
| (10) | Perfume | q.s. |

The ingredients (7) and (8) were charged into a still and heated to 80° C. to 90° C. and the ingredients (5) and (6) were added thereto. Then, the ingredients (1) to (4) were added and uniformly dispersed. After degassing, the component (10) was added and the resultant mixture was gently stirred. The mixture having a temperature of 80° C. was cast into a container and cooled to room temperature. Thus, the desired UV preventive stick was obtained.

COMPARATIVE EXAMPLE 12-6

The UV preventive stick was prepared in the same manner as in Example 12-5, except that the modified titanium dioxide was replaced by the untreated titanium dioxide.

The stick obtained in Example 12-5 was superior to that of Comparative Example 12-6 in the dispersibility of the titanium dioxide, the cosmetic finish, and in the suntan preventive effect.

EXAMPLE 12-6

Preparation of Lipstick

The lipstick having the following composition was prepared:

|  | Ingredient | Parts |
|---|---|---|
| (1) | Hydrocarbon wax | 3 |
| (2) | Carnanba wax | 1 |
| (3) | Glyceryl isostearate | 40 |
| (4) | Liquid paraffin | 45.8 |
| (5) | Modified titanium dioxide of Example 4-1 | 4 |
| (6) | h-BN (3μ) | 3 |
| (7) | Organic pigment | 3 |
| (8) | Perfume | 0.2 |

The ingredients (1) to (3) and (4) were dissolved at 85° C. and the ingredients (5), (6), and (7) were added thereto, while stirring. Finally the ingredient (8) was mixed while stirring. The resultant mixture was packed into a container. Thus, the desired lipstick having excellent dispersibility was obtained.

We claim:

1. In a cosmetic composition comprising a cosmetic base and a powder, the improvement wherein such powder comprises a modified powder having a silicone polymer film coated on substantaily the entire surface thereof, said powder being produced by bringing at least one silicone compound, in the form of vapor, having the general formula (I):

$$(R^1HSiO)_a(R^2R^3SiO)_b(R^4R^5R^6SiO_{\frac{1}{2}})_c \qquad (I)$$

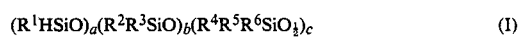

wherein $R^1$, $R^2$, and $R^3$ represent, independently, hydrogen, a hydrocarbon residue having 1 to 10 carbon atoms or a hydrocarbon residue having 1 to 10 carbon atoms and substituted with at least one halogen atom, provided that $R^1$, $R^2$, $R^3$ are not hydrogen at the same time, $R^4$, $R^5$, and $R^6$ represent, independently, hydrogen, a hydrocarbon residue having 1 to 10 carbon atoms or a hydrocarbon residue having 1 to 10 carbon atoms and substituted with at least one halogen atom, a is zero or an integer of 1 or more, b is zero or an integer of 1 or more, and c is zero or 2, provided that c is 2 when a and b are simultaneously zero and a +b is an integer of 3 or more when c is zero, into contact with the powder having on the usrface thereof an active site capable of catalytically polymerizing a silicone compound having a siloxane bond (Si-O-Si) or a hydrosilyl group (Si H), whereby the silicone compound is polymerized on substantially the entire surface of the powder.

2. A composition as claimed in claim 1, wherein the silicone polymer film has a weight-average molecular weight of more than 200,000.

3. A composition as claimed in claim 1, wherein the silicone polymer film has a network structure having a

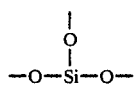

unit derived from the polymerization of Si-H moieties in amount of 20% or more of the total Si atoms contained in the polymer film.

4. A composition as claimed in claim 1, the silicone compound is a cyclic silicone compound having the general formula in which a is 3 to 7 and b and c are zero.

5. A composition as claimed in claim 1, wherein the thickness of the silicone polymer film is 3 to 20Å.

6. A composition as claimed in claim 1, wherein the silicone compound is brought into contact with the powder having the active sites on the surface thereof at a temperature of 120° C. or less in a closed chamber in such a manner that the vaporized silicone compound is deposited under a molecular state on the surface of the powder.

7. A composition as claimed in claim 6, wherein the silicone compound is brought into contact with the powder under a of 200 mmHg or less.

8. A composition as claimed in claim 1, wherein the silicone compound is brought into contact with the powder having the active sites on the surface thereof by feeding a gas mixture of the silicone compound (I) and a carrier gas.

9. A composition as claimed in claim 8, wherein the silicone compound is brought into contact with the powder at a temperature of 120° C. or less.

10. A composition as claimed in claim 1, wherein said powder is an inorganic pigment.

11. A compostion as claimed in claim 1, said powder is a metallic oxide or hydroxide.

12. A composition as claimed in claim 1, wherein said powder is a mica.

13. A composition as claimed in claim 1, wherein said powder is an organic pigment.

14. A composition as claimed in claim 1, wherein said powder is a pearlescent pigment.

15. A composition as claimed in claim 1, wherein said powder is a mineral silicate.

16. A composition as claimed in claim 1, wherein said powder is a porous material.

17. a composition as claimed in claim 1, werein said powder is a carbon.

18. A composition as claimed in claim 1, wherein said powder is a metal.

19. A composition as claimed in claim 1, wherein said powder is a composite powder.

20. A composition according to claim 1, wherein silicone polymer film has a weight-average molecular weight of more than 200,000 and its thickness is 3 to 20 Å.

21. A composition according to claim 1, wherein the powder is an inorganic pigment, metallic oxide or hydroxide, a mica, an organic pigment, a pearlescent pigment, a mineral silicate, a carbon, a metal or a composite powder.

* * * * *

UNITED STATES PATENT AND TRADEMARK OFFICE
CERTIFICATE OF CORRECTION

PATENT NO. : 4,801,445
DATED : January 31, 1989
INVENTOR(S) : Hiroshi Fukui, et al It is certified that error appears in the above-identified patent and that said Letters Patent is hereby corrected as shown below:

| | |
|---|---|
| Col. 4, line 29 | Delete "silrcates" and substitute --silicates-- |
| Col. 15, line 21 | Delete "tianium" and substitute --titanium-- |
| Col. 33, line 63 | Delete "heatng" and substitute --heating-- |
| Col. 37, line 25 | Delete "desire" and substitute --desired-- |
| Col. 37, line 33 | Delete "powde" and substitute --powder-- |
| Col. 40, line 31 | Delete "substantailly" and substitute --substantially-- |
| Col. 40, line 51 | Delete "usrface" and substitute --surface-- |
| Col. 41, line 1 | Insert --an-- before "amount" |
| Col. 41, line 17 | Insert --pressure-- after "a" |

Signed and Sealed this

Thirtieth Day of January, 1990

Attest:

JEFFREY M. SAMUELS

Attesting Officer     Acting Commissioner of Patents and Trademarks